United States Patent
Candau

(10) Patent No.: US 7,166,274 B2
(45) Date of Patent: Jan. 23, 2007

(54) SYNERGISTICALLY HIGH SPF PHOTOPROTECTIVE UV-SCREENING COMPOSITIONS COMPRISING INSOLUBLE ORGANIC SUNSCREEN PARTICLES/DIARYLBUTADIENE COMPOUNDS

(75) Inventor: Didier Candau, Bièvres (FR)

(73) Assignee: L'Oreal, Paris (FR)

( * ) Notice: Subject to any disclaimer, the term of this patent is extended or adjusted under 35 U.S.C. 154(b) by 574 days.

(21) Appl. No.: 10/463,328

(22) Filed: Jun. 18, 2003

(65) Prior Publication Data

US 2004/0047820 A1    Mar. 11, 2004

Related U.S. Application Data

(63) Continuation of application No. PCT/FR01/03637, filed on Nov. 20, 2001.

(30) Foreign Application Priority Data

Dec. 18, 2000   (FR) ................... 00 16520

(51) Int. Cl.
| | |
|---|---|
| *A61Q 17/00* | (2006.01) |
| *A61Q 17/04* | (2006.01) |
| *A61Q 19/00* | (2006.01) |
| *A61K 8/00*  | (2006.01) |

(52) U.S. Cl. .................. 424/59; 424/60; 424/400; 424/401

(58) Field of Classification Search .......... 424/59, 424/60, 400, 401
See application file for complete search history.

(56) References Cited

U.S. PATENT DOCUMENTS

| | | | |
|---|---|---|---|
| 5,166,355 A * | 11/1992 | Leistner et al. ........... 548/260 |
| 5,237,071 A * | 8/1993  | Leistner et al. ........... 548/260 |
| 5,362,881 A * | 11/1994 | Leistner et al. ........... 548/260 |
| 5,687,521 A * | 11/1997 | Carlson et al. ............ 52/308 |
| 6,093,385 A   | 7/2000  | Habeck et al. |
| 6,193,960 B1  | 2/2001  | Metzger et al. |
| 6,238,649 B1  | 5/2001  | Habeck et al. |
| 6,368,577 B1  | 4/2002  | Kropf et al. |
| 6,409,998 B1  | 6/2002  | Candau et al. |
| 6,436,373 B1  | 8/2002  | Habeck et al. |
| 6,746,666 B1  | 6/2004  | Luther |
| 2002/0004034 A1 | 1/2002 | Heidenfelder et al. |
| 2002/0010179 A1 | 1/2002 | Richard et al. |

FOREIGN PATENT DOCUMENTS

| | | |
|---|---|---|
| DE | 197 46 654 A1 | 2/1999 |
| DE | 197 55 649 A1 | 6/1999 |
| EP | 0 893 119 B1 | 1/1999 |
| EP | 0967200 B1   | 12/1999 |
| EP | 1 008 586 B1 | 6/2000 |
| EP | 1 093 796 B1 | 4/2001 |
| EP | 1 133 981 A2 | 9/2001 |
| GB | 2 303 549 A  | 2/1997 |
| WO | 95/22959 A2  | 8/1995 |
| WO | 98/25922 A1  | 6/1998 |
| WO | 99/66896 A1  | 12/1999 |
| WO | 00/35415 A1  | 6/2000 |
| WO | 00/78277 A1  | 12/2000 |

\* cited by examiner

*Primary Examiner*—Shelley A. Dodson
(74) *Attorney, Agent, or Firm*—Buchanan Ingersoll & Rooney PC

(57) ABSTRACT

Topically applicable high SPF cosmetic/dermatological UV-screening compositions suited for the photoprotection of the skin and/or hair, comprise (a) particulates of at least one insoluble organic UV-screening agent having a particle size ranging from 10 nm to 5 μm, as a first screening agent, and (b) at least one 4,4-diarylbutadiene compound, as a second screening agent, formulated into a topically applicable, cosmetically/dermatologically acceptable vehicle therefor.

68 Claims, No Drawings

SYNERGISTICALLY HIGH SPF PHOTOPROTECTIVE UV-SCREENING COMPOSITIONS COMPRISING INSOLUBLE ORGANIC SUNSCREEN PARTICLES/DIARYLBUTADIENE COMPOUNDS

CROSS-REFERENCE TO PRIORITY/PCT APPLICATIONS

This application claims priority under 35 U.S.C. § 119 of FR 00/16520, filed Dec. 18, 2000, and is a continuation of PCT/FR01/03637, filed Nov. 20, 2001 and designating the United States (published in the French language on Jun. 27, 2002 as WO 02/49597 A2; the title and abstract were also published in English), both hereby expressly incorporated by reference.

BACKGROUND OF THE INVENTION

1. Technical Field of the Invention

The present invention relates to novel cosmetic compositions for topical application, more particularly in a regime or regimen for the photoprotection of the skin and/or hair against ultraviolet radiation (compositions more simply referred to hereinafter as antisun compositions), and to their use in the abovementioned cosmetic regime/regimen. More specifically still, it relates to antisun compositions comprising, in a cosmetically acceptable vehicle, a combination of at least two specific screening agents, namely, on the one hand, an insoluble organic UV-screening agent with a particle size ranging from 10 nm to 5 μm and, on the other hand, a 4,4-diarylbutadiene compound.

2. Description of Background/Related/Prior Art

It is known that light radiation with wavelengths of between 280 nm and 400 nm makes possible browning of the human epidermis and that rays with wavelengths of between 280 and 320 nm, known under the name of UV-B, cause erythemas and skin burns which may be harmful to the development of natural tanning; this UV-B radiation must therefore be screened out.

It is also known that UV-A rays, with wavelengths of between 320 and 400 nm, which cause browning of the skin, are capable of bringing about a detrimental change in the latter, in particular in the case of sensitive skin or of skin continually exposed to solar radiation. UV-A rays cause in particular a loss in the elasticity of the skin and the appearance of wrinkles, resulting in premature ageing. They promote the triggering of the erythemal reaction or accentuate this reaction in some subjects and can even be the cause of phototoxic or photoallergic reactions. It is therefore desirable also to screen out UV-A radiation.

Numerous cosmetic compositions intended for the photoprotection (UV-A and/or UV-B) of the skin have been provided to date.

These antisun compositions exist fairly often in the form of an emulsion of oil-in-water type (that is to say, a cosmetically acceptable vehicle composed of a continuous aqueous dispersing phase and of a noncontinuous oily dispersed phase) which comprises, at various concentrations, one or more conventional, lipophilic and/or hydrophilic, organic screening agents capable of selectively absorbing harmful UV radiation, these screening agents (and their amounts) being selected according to the sun protection factor desired, the sun protection factor (SPF) being expressed mathematically by the ratio of the dose of UV radiation necessary to reach the erythemogenic threshold with the UV-screening agent to the dose of UV radiation necessary to reach the erythemogenic threshold without UV-screening agent.

Suntan compositions based on 4,4-diarylbutadienes which can comprise other additional screening agents, such as methylene bis-benzotriazolyl tetramethylbutylphenol, are known from EP-0-967,200, DE-197,46,654, DE-197,55-649, EP-1-008,586, DE-100,07,017, EP-1-133,980 and EP-1-133,981.

SUMMARY OF THE INVENTION

After much research carried out in the abovementioned field of photoprotection, it has now unexpectedly and surprisingly been determined that the combination, in proportions within well-defined limits, of two specific sunscreens already known per se in the state of the art makes it possible, due to a notable synergistic effect, to obtain antisun compositions exhibiting protection factors which are markedly improved and in any case much higher than those which can be obtained with either of the screening agents used on its own.

This discovery is the basis of the present invention.

Thus, the present invention features novel cosmetic compositions for topical use application, in particular in a regime or regimen for the photoprotection of the skin and/or hair, comprising, formulated into a cosmetically acceptable vehicle:

(a) at least one insoluble organic UV-screening agent with a particle size ranging from 10 nm to 5 μm, as a first screening agent, and (b) at least one 4,4-diarylbutadiene compound, as a second screening agent.

The present invention also features the use of such compositions in the manufacture of cosmetic compositions intended for the protection of the skin and/or hair against ultraviolet radiation, in particular solar radiation.

This invention also features the use of a 4,4-diarylbutadiene compound in the manufacture of cosmetic or dermatological compositions intended for the protection of the skin and/or hair against ultraviolet radiation, in particular solar radiation, comprising at least one insoluble organic UV-screening agent with a particle size ranging from 10 nm to 5 μm, for the purpose of producing a synergistic effect with regard to the sun protection factors conferred.

DETAILED DESCRIPTION OF BEST MODE AND SPECIFIC/PREFERRED EMBODIMENTS OF THE INVENTION

The term "insoluble UV-screening agent" within the meaning of the present invention is understood to mean particulates of any organic or inorganic UV-screening agent having a solubility in water of less than 0.1% by weight and a solubility of less than 1% by weight in the majority of organic solvents, such as liquid paraffin, fatty alcohol benzoates and fatty acid triglycerides, for example Miglyol® 812 sold by Dynamit Nobel. This solubility, defined at 70° C. as the amount of product in solution in the solvent at equilibrium with an excess of solid in suspension, can easily be evaluated in the laboratory.

The term "4,4-diarylbutadiene" according to the invention is understood to mean any molecule comprising at least one 4,4-diarylbutadiene chromophoric group. The latter can exist in the form of a single compound, of an oligomer or of a polymer having, on the chain, grafts comprising the chromophoric group.

Other characteristics, aspects, embodiments and advantages of the present invention will become apparent on reading the detailed description which will follow.

Generally, the insoluble UV-screening agent and the 4,4-diarylbutadiene compound are present in the said compositions in a proportion producing a synergistic activity with regard to the sun protection factors conferred.

The insoluble organic UV-screening agents according to the invention have a mean particle size which varies from 10 nm to 5 µm and more preferably from 10 nm to 2 µm and more particularly from 20 nm to 2 µm.

The insoluble organic screening agents according to the invention can be converted to the desired particulate form by any ad hoc means, such as, in particular, dry milling or milling in a solvent medium, sieving, atomization, micronization or spraying.

The insoluble organic screening agents according to the invention in the micronized form can be obtained in particular by a process of milling an insoluble organic UV-screening agent in the form of coarse particles in the presence of an appropriate surfactant which makes it possible to improve the dispersion of the particles thus obtained in cosmetic formulations.

An example of a process for the micronization of insoluble organic screening agents is described in GB-A-2,303,549 and EP-A-893,119, which form an integral part of the description. The milling device used according to these documents can be an airjet mill, bead mill, vibration mill or hammer mill and preferably a mill with high-speed stirring or an impact mill and more particularly a rotary bead mill, a vibrating mill, a tube mill or a rod mill.

According to this specific process, use is made, as surfactants for the milling of the said screening agents, of alkypolyglucosides with the structure $C_nH_{2n+1}O(C_6H_{10}O_5)_xH$ in which n is an integer from 8 to 16 and x is the mean degree of polymerization of the $(C_6H_{10}O_5)$ unit and varies from 1.4 to 1.6. They can be chosen from $C_1$–$C_{12}$ esters of a compound with the structure $C_nH_{2n+1}O(C_6H_{10}O_5)_xH$ and more specifically an ester obtained by reaction of a $C_1$–$C_{12}$ carboxylic acid, such as formic, acetic, propionic, butyric, sulfosuccinic, citric or tartaric acid, with one or more free OH functional groups on the glucoside unit $(C_6H_{10}O_5)$. The said surfactants are generally used at a concentration ranging from 1% to 50% by weight and more preferably from 5% to 40% by weight with respect to the insoluble screening agent in its micronized form.

The insoluble organic UV-screening agents in accordance with the invention can be chosen in particular from organic UV-screening agents of the oxalanilide type, of the triazine type, of the benzotriazole type; of the vinyl amide type; of the cinnamamide type; of the type comprising one or more benzazole and/or benzofuran or benzothiophene groups or of the indole type; of the aryl vinylene ketone type; of the phenylenebis(benzoxazinone) derivative type; or of the acrylonitrile amide, sulfonamide or carbamate derivative type.

In the sense in which it is used in the present invention, the term benzazole simultaneously encompasses benzothiazoles, benzoxazoles and benzimidazoles.

Mention may be made, among UV-screening agents of the oxalanilide type in accordance with the invention, of those corresponding to the structure:

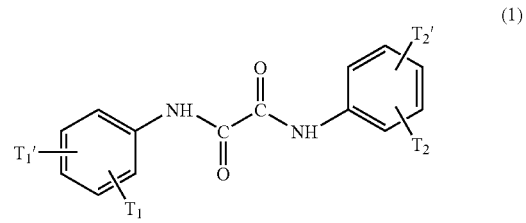

in which $T_1$, $T'_1$, $T_2$ and $T'_2$, which are identical or different, denote a $C_1$–$C_8$ alkyl radical or a $C_1$–$C_8$ alkoxy radical. These compounds are described in WO 95/22959.

Mention may be made, as examples, of the commercial products Tinuvin 315 and Tinuvin 312, sold by Ciba-Geigy, with the respective structures:

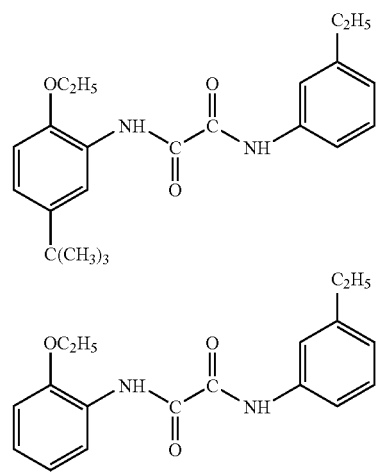

Mention may also be made, among insoluble UV-screening agents of the triazine type in accordance with the invention, of those corresponding to the following formula (2):

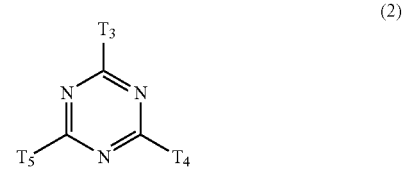

in which $T_3$, $T_4$ and $T_5$ are independently phenyl, phenoxy or pyrrolo, in which the phenyl, phenoxy or pyrrolo groups are unsubstituted or substituted by one, two or three substituents chosen from OH, $C_1$–$C_{18}$ alkyl or $C_1$–$C_{18}$ alkoxy, $C_1$–$C_{18}$ carboxyalkyl, $C_5$–$C_8$ cycloalkyl, a methylbenzylidenecamphor group, a —(CH═CH)$_n$(CO)—OT$_6$ group, with $T_6$ either $C_1$–$C_{18}$ alkyl or cinnamyl, and n has the value 0 or 1.

These compounds are described in WO 97/03642, GB-2-286,774, EP-743 309, WO 98/22447 and GB-2-319,523 (which form an integral part of the content of the description).

Mention may also be made, among UV-screening agents of the triazine type in accordance with the invention, of insoluble s-triazine derivatives carrying benzalmalonate and/or phenylcyanoacrylate groups, such as those described in EP-A-0-790,243 (which forms an integral part of the content of the description).

Mention will more particularly be made, among these insoluble UV-screening agents of the triazine type, of the following compounds:
  2,4,6-tris(diethyl 4'-aminobenzalmalonate)-s-triazine,
  2,4,6-tris(diisopropyl 4'-aminobenzalmalonate)-s-triazine,
  2,4,6-tris(dimethyl 4'-aminobenzalmalonate)-s-triazine,
  2,4,6-tris(ethyl α-cyano-4-aminocinnamate)-s-triazine.

Mention may also be made, among UV-screening agents of the triazine type in accordance with the invention, of insoluble s-triazine derivatives carrying benzotriazole and/or benzothiazole groups, such as those described in WO 98/25922 (which forms an integral part of the content of the description).

Mention may more particularly be made, among these compounds, of:
  2,4,6-tris[(3'-(benzotriazol-2-yl)-2'-hydroxy-5'-methyl)phenylamino]-s-triazine,
  2,4,6-tris[(3'-(benzotriazol-2-yl)-2'-hydroxy-5'-tert-octyl)phenylamino]-s-triazine.

Mention may be made, among insoluble organic UV-screening agents of the benzotriazole type in accordance with the invention, of those of following formula (3) as described in WO 95/22959 (which forms an integral part of the content of the description):

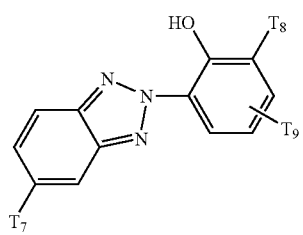

(3)

in which $T_7$ denotes a hydrogen atom or a $C_1$–$C_{18}$ alkyl radical; $T_8$ and $T_9$, which are identical or different, denote a $C_1$–$C_{18}$ alkyl radical optionally substituted by a phenyl.

Mention may be made, as examples of compounds of formula (3), of the commercial products Tinuvin 328, 320, 234 and 350 from Ciba-Geigy, with the following structures:

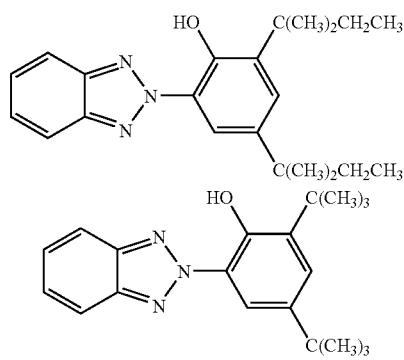

-continued

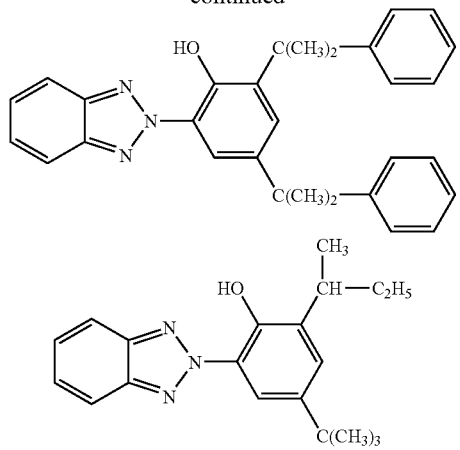

Mention may be made, among insoluble organic UV-screening agents of the benzotriazole type in accordance with the invention, of the compounds as described in U.S. Pat. Nos. 5,687,521, 5,373,037 and 5,362,881 and in particular [2,4'-dihydroxy-3-(2H-benzotriazol-2-yl)-5-(1,1,3,3-tetramethylbutyl)-2'-(n-octoxy)-5'-benzoyl]diphenylmethane, sold under the name Mixxim PB30 by Fairmount Chemical, with the structure:

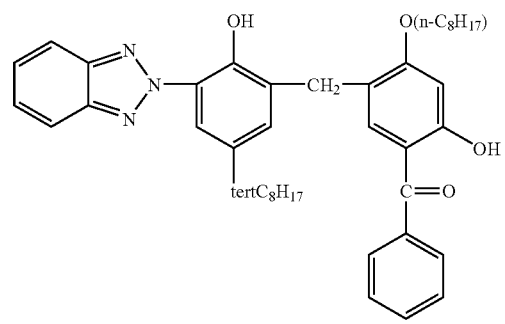

Mention may be made, among insoluble organic UV-screening agents of the benzotriazole type in accordance with the invention, of methylenebis-(hydroxyphenylbenzotriazole) derivatives with the following structure:

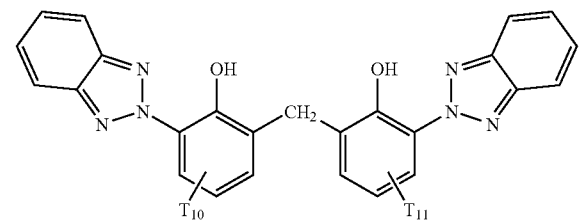

(4)

in which the $T_{10}$ and $T_{11}$ radicals, which are identical or different, denote a $C_1$–$C_{18}$ alkyl radical which can be substituted by one or more radicals chosen from a $C_1$–$C_4$ alkyl radical, a $C_5$–$C_{12}$ cycloalkyl radical or an aryl residue. These compounds are known per se and are described in U.S. Pat.

Nos. 5,237,071, 5,166,355, GB-A-2-303,549, DE-197,26, 184 and EP-A-893,119 (which form an integral part of the description).

In the formula (4) defined above: the $C_1$–$C_{18}$ alkyl groups can be linear or branched and are, for example, methyl, ethyl, n-propyl, isopropyl, n-butyl, isobutyl, tert-butyl, tert-octyl, n-amyl, n-hexyl, n-heptyl, n-octyl, isooctyl, n-nonyl, n-decyl, n-undecyl, n-dodecyl, tetradecyl, hexadecyl or octadecyl; the $C_5$–$C_{12}$ cycloalkyl groups are, for example, cyclopentyl, cyclohexyl or cyclooctyl; and the aryl groups are, for example, phenyl or benzyl.

Preference is more particularly given, among the compounds of formula (4), to those with the following structures:

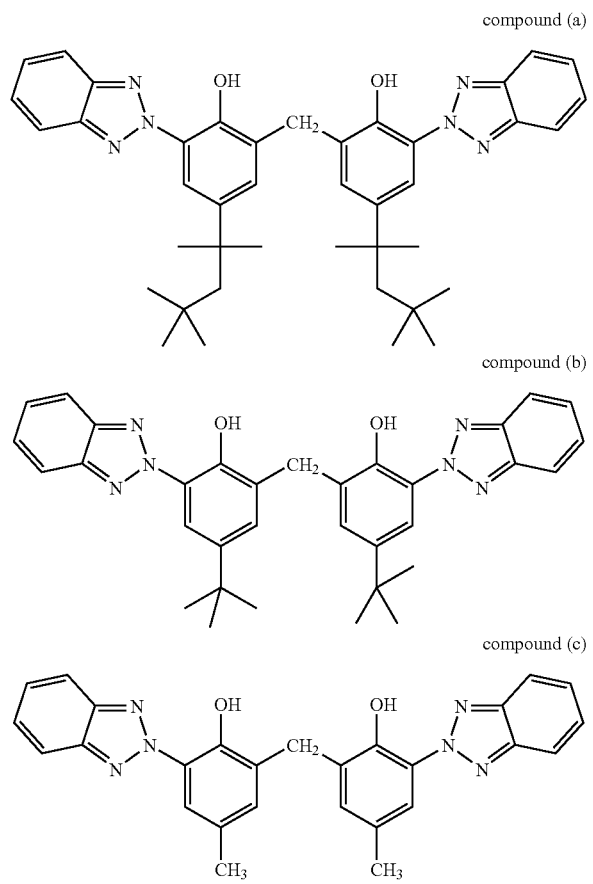

compound (a)

compound (b)

compound (c)

Compound (a), with the nomenclature 2,2'-methylenebis[6-(2H-benzotriazol-2-yl)-4-(1,1,3,3-tetramethylbutyl)phenol], is sold in the micronized form under the name Tinosorb M by Ciba Specialty Chemicals.

Compound (c), with the nomenclature 2,2'-methylenebis[6-(2H-benzotriazol-2-yl)-4-methyl-phenol], is sold in the solid form under the name Mixxim BB/200 by Fairmount Chemical.

Mention may be made, among insoluble organic screening agents of the vinyl amide type, of, for example, the compounds with the following formula which are described in WO 95/22959 (which forms an integral part of the content of the description):

$$T_{12}-(Y)_r-C(=O)-C(T_{13})=C(T_{14})-N(T_{15})(T_{16}) \qquad (5)$$

in which $T_{12}$ is a $C_1$–$C_{18}$, preferably $C_1$–$C_5$, alkyl radical or a phenyl group optionally substituted by one, two or three radicals chosen from OH, a $C_1$–$C_{18}$ alkyl radical, a $C_1$–$C_8$ alkoxy radical, or a group —C(=O)—$OT_{17}$ where $T_{17}$ is a $C_1$–$C_{18}$ alkyl; $T_{13}$, $T_{14}$, $T_{15}$ and $T_{16}$, which are identical or different, denote a $C_1$–$C_{18}$, preferably $C_1$–$C_5$, alkyl radical or a hydrogen atom; Y is N or O and r has the value 0 or 1.

Mention will more particularly be made, among these compounds, of:
- 4-octylamino-3-penten-2-one;
- ethyl 3-octylamino-3-butenoate;
- 3-octylamino-1-phenyl-2-buten-1-one;
- 3-dodecylamino-1-phenyl-2-buten-1-one.

Mention may also be made, among insoluble organic screening agents of the cinnamamide type in accordance with the invention, of the compounds as described in WO 95/22959 (which forms an integral part of the content of the description) and corresponding to the following structure:

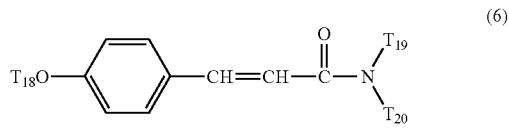

(6)

in which $OT_{18}$ is a hydroxyl or $C_1$–$C_4$ alkoxy radical, preferably a methoxy or ethoxy radical; $T_{19}$ is hydrogen or $C_1$–$C_4$ alkyl, preferably methyl or ethyl; $T_{20}$ is a —(CONH)$_s$-phenyl group where s has the value 0 or 1 and the phenyl group can be substituted by one, two or three groups chosen from OH, $C_1$–$C_{18}$ alkyl, $C_1$–$C_8$ alkoxy, or a —C(=O)—$OT_{21}$ group where $T_{21}$ is a $C_1$–$C_{18}$ alkyl and more preferably $T_{21}$ is a phenyl, 4-methoxyphenyl or phenylaminocarbonyl group.

Mention may also be made of cinnamamide dimers, such as those described in U.S. Pat. No. 5,888,481, such as, for example, the compound with the structure:

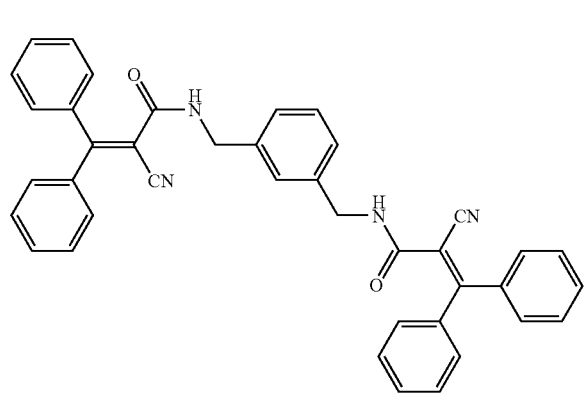

Mention may be made, among insoluble organic screening agents of the benzazole type, of those corresponding to one of the following formulae:

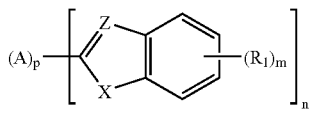

(7)

-continued (8)

(9)

in which each of the X symbols independently represents an oxygen or sulfur atom or an $NR_2$ group, each of the Z symbols independently represents a nitrogen atom or a CH group, each of the $R_1$ symbols independently represents an OH group, a halogen atom, a linear or branched $C_{1-8}$ alkyl group, optionally comprising a silicon atom, or a linear or branched $C_{1-8}$ alkoxy group, each of the numbers m independently has the value 0, 1 or 2, n represents an integer between 1 and 4 inclusive, p is equal to 0 or 1, each of the numbers q is independently equal to 0 or 1, each of the $R_2$ symbols independently represents a hydrogen atom or a benzyl or linear or branched $C_{1-8}$ alkyl group, optionally comprising a silicon atom, A represents a radical with a valency n chosen from those of formulae:

(a)

(b)

(c)

(d)

(e)

(f)

(g)

(h)

(i)

(j)

(k)

(l)

(m)

(n)

(o)

in which each of the $R_3$ symbols independently represents a halogen atom or a linear or branched $C_{1-4}$ alkyl or alkoxy group or a hydroxyl group, $R_4$ represents a hydrogen atom or a linear or branched $C_{1-4}$ alkyl group, c=0–4, d=0–3, e=0 or 1 and f=0–2.

These compounds are described in particular in DE-676,103 and CH-350,763, U.S. Pat. Nos. 5,501,850, 5,961,960, EP-0-669,323, U.S. Pat. Nos. 5,518,713, 2,463,264, the paper in J. Am. Chem. Soc., 79, 5706–5708, 1957, the paper in J. Am. Chem. Soc., 82, 609–611, 1960, EP-0-921,126 and EP-712,855.

Mention may be made, as examples of preferred compounds of formula (7) of the family of the 2-arylbenzazoles, of 2-(benzoxazol-2-yl)-4-methylphenol, 2-(1H-benzimidazol-2-yl)-4-methoxyphenol or 2-(benzothiazol-2-yl)phenol, it being possible for these compounds to be prepared, for example, according to the processes described in CH-350,763.

Mention will be made, as examples of preferred compounds of formula (7) of the family of the benzimidazolylbenzazoles, of 2,2'-bisbenzimidazole, 5,5',6,6'-tetramethyl-2,2'-bisbenzimidazole, 5,5'-dimethyl-2,2'-bisbenzimidazole, 6-methoxy-2,2'-bisbenzimidazole, 2-(1H-benzimidazol-2-yl)-benzothiazole, 2-(1H-benzimidazol-2-yl)benzoxazole and N,N'-dimethyl-2,2'-bisbenzimidazole, it being possible for these compounds to be prepared according to the procedures described in U.S. Pat. Nos. 5,961,960 and 2,463,264.

Mention will be made, as examples of preferred compounds of formula (7) of the family of the phenylenebenzazoles, of 1,4-phenylenebis(2-benzoxa-zolyl), 1,4-phenylenebis(2-benzimidazolyl), 1,3-phenylenebis(2-benzoxazolyl), 1,2-phenylene-bis(2-benzoxazolyl), 1,2-phenylenebis(benzimidazolyl), 1,4-phenylenebis(N-(2-ethylhexyl)-2-benzimidazolyl) and 1,4-phenylenebis(N-trimethylsilylmethyl-2-benzimida-zolyl), it being possible for these compounds to be prepared according to the procedures described in U.S. Pat. No. 2,463,264 and in the publications J. Am. Chem. Soc., 82, 609 (1960) and J. Am. Chem. Soc., 79, 5706–5708 (1957).

Mention will be made, as examples of preferred compounds of formula (7) of the family of the benzofuranylbenzoxazoles, of 2-(2-benzofuranyl)benzoxazole, 2-(benzofuranyl)-5-methylbenzoxazole and 2-(3-methyl-2-benzofuranyl)benzoxazole, it being possible for these compounds to be prepared according to the procedures described in U.S. Pat. No. 5,518,713.

Mention may be made, as preferred compounds of formula (8), of, for example, 2,6-diphenyl-1,7-di-hydrobenzo[1,2-d;4,5-d']diimidazole, corresponding to the formula

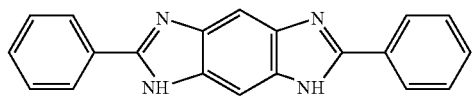

or 2,6-distyryl-1,7-dihydrobenzo[1,2-d;4,5-d']di-imidazole or 2,6-di(p-tert-butylstyryl)-1,7-dihydro-benzo[1,2-d;4,5-d']diimidazole, which compounds can be prepared according to EP-0-669,323.

Mention may be made, as preferred compound of formula (9), of 5,5'-bis(2-phenylbenzimidazole) of formula:

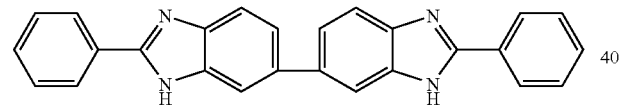

the preparation of which is described in J. Chim. Phys., 64, 1602 (1967).

Preference is very particularly given, among these insoluble organic compounds which screen out UV radiation, to 2-(1H-benzimidazol-2-yl)benzoxazole, 6-methoxy-2,2'-bisbenzimidazole, 2-(1H-benzimidazol-2-yl)benzothiazole, 1,4-phenylenebis(2-benzoxazolyl), 1,4-phenylenebis(2-benzimidazolyl), 1,3-phenylene-bis(2-benzoxazolyl), 1,2-phenylenebis(2-benzoxazolyl), 1,2-phenylenebis(2-benzimidazolyl) and 1,4-phenylene-bis(N-trimethylsilylmethyl-2-benzimidazolyl).

Mention may be made, among insoluble organic screening agents of the aryl vinylene ketone type, of those corresponding to either of the following formulae (10) and (11):

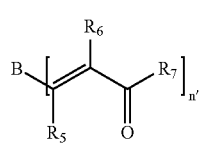

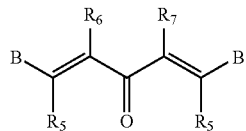

in which:
n'=1 or 2,
B, in the formula (10) when n'=1 or in the formula (11), is an aryl radical chosen from the following formulae (a') to (d') or, in the formula (10) when n'=2, is a radical chosen from the following formulae (e') to (h'):

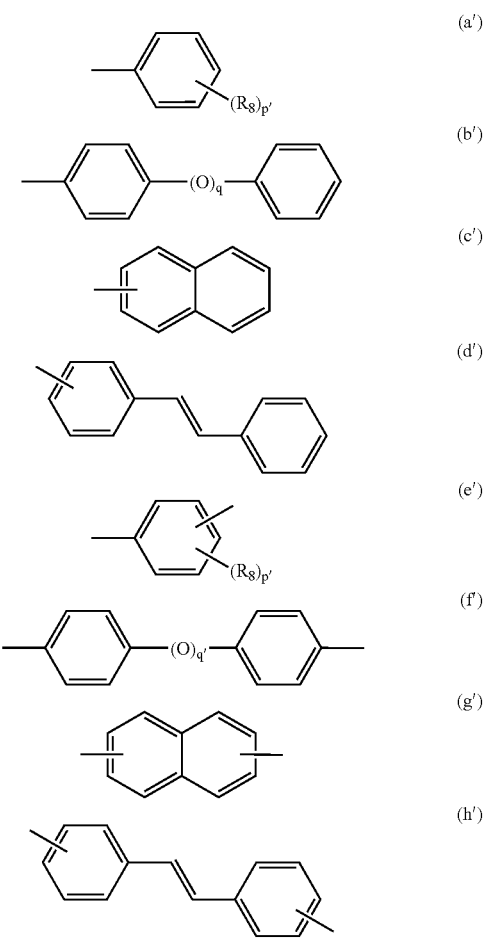

in which:
each of the $R_8$ symbols independently represents an OH group, a halogen atom, a linear or branched $C_{1-6}$ alkyl group optionally comprising a silicon atom, a linear or branched $C_{1-6}$ alkoxy group optionally comprising a silicon atom, a linear or branched $C_{1-5}$ alkoxycarbonyl group, or a linear or branched $C_{1-6}$ alkylsulfonamide group optionally comprising a silicon atom or an amino acid functional group,
p' represents an integer ranging from 0 to 4, inclusive,
q' represents 0 or 1,
$R_5$ represents hydrogen or an OH group, $R_6$ represents hydrogen, a linear or branched $C_{1-6}$ alkyl group optionally comprising a silicon atom, a cyano group, a $C_{1-6}$ alkylsulfonyl group or a phenylsulfonyl group, $R_7$ represents a linear or branched $C_{1-6}$ alkyl group optionally comprising a silicon atom or a phenyl group which can form a bicycle and which is optionally substituted by one or two $R_4$ radicals, or $R_6$ and $R_7$ together form a monocyclic, bicyclic or tricyclic $C_{2-10}$ hydrocarbonaceous residue, optionally interrupted by one or more nitrogen, sulfur and oxygen atoms and which can comprise another carbonyl, and optionally substituted by a linear or branched $C_1$–$C_8$ alkylsulfonamide group, and optionally comprising a silicon atom or an amino acid functional group; provided that, when n'=1, $R_6$ and $R_7$ do not form a camphor nucleus.

Mention may be made, as examples of compounds of formula (10) in which n'=1, which are insoluble, which screen out UV radiation and which have a mean particle size of between 10 nm and 5 µm, of the following families:

compounds of the styryl ketone type as described in JP 04 134 042, such as 1-(3,4-dimethoxy-phenyl)-4,4-dimethyl-pent-1-en-3-one:

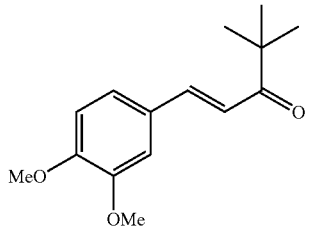

compounds of the benzylidenecineole type, such as those described in the paper by E. Mariani et al., 16th IFSCC Congress, New York (1990), for example 1,3,3-trimethyl-5-(4-methoxybenzylidene)-2-oxa-bicyclo[2.2.2]octan-6-one:

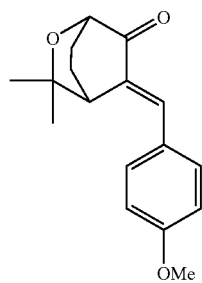

compounds of the benzylidenechromanone type, such as those described in JP 04 134 043, for example 3-(4-methoxybenzylidene)-2,3,4a,8a-tetrahydro-chromen-4-one:

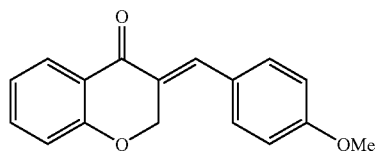

compounds of the benzylidenethiochromanone type, such as those described in JP 04 134 043, for example 3-(4-methoxybenzylidene)-2,3,4a,8a-tetrahydro-chromen-4-thione:

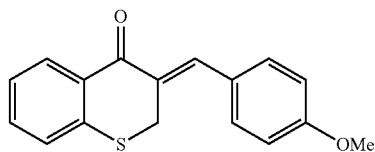

compounds of the benzylidenequinuclidinone type, such as those described in EP-0-576,974, for example 4-methoxybenzylidene-1-azabicyclo[2.2.2]octan-3-one:

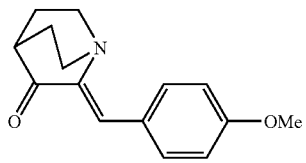

compounds of the benzylidenecycloalkanone type, such as those described in FR-2-395,023, for example 2-(4-methoxybenzylidene)cyclopentanone and 2-(4-methoxybenzylidene)cyclohexanone:

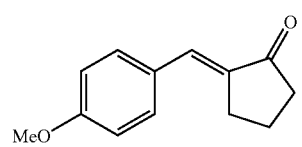

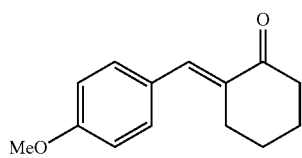

compounds of the benzylidenehydantoin type, such as those described in JP 01 158 090, for example 5-(3,4-dimethoxybenzylidene)imidazolidine-2,4-dione:

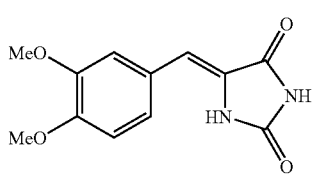

compounds of the benzylideneindanone type, such as those described in JP 04 134 043, for example 2-(4-methoxybenzylidene)indan-1-one:

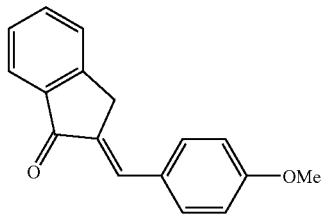

compounds of the benzylidenetetralone type, such as those described in JP 04 134 043, for example 2-(4-methoxybenzylidene)-3,4-dihydro-2H-naphthalen-1-one;

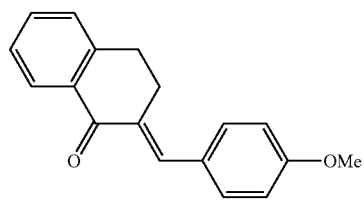

compounds of the benzylidenefuranone type, such as those described in EP-0-390,683, for example 4-(4-methoxybenzylidene)-2,2,5,5-tetramethyldihydrofuran-3-one:

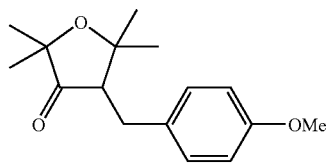

compounds of the benzylidenebenzofuranone type, such as those described in JP 04 134 041, for example 2-benzylidenebenzofuran-3-one:

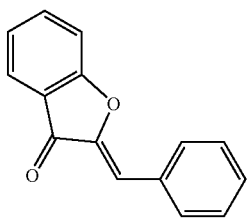

compounds of the benzylideneindanedione type, such as 2-(3,5-di(tert-butyl)-4-hydroxybenzylidene)indane-1,3-dione:

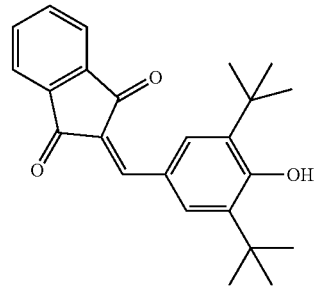

compounds of the benzylidenebenzothiofuranone type, such as those described in JP 04,134,043, for example 2-benzylidenebenzo[b]thiophen-3-one:

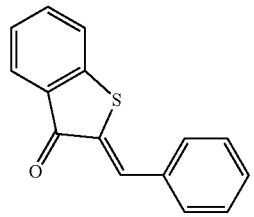

compounds of the benzylidenebarbituric type, such as 5-(4-methoxybenzylidene)-1,3-dimethylpyrimidine-2,4,6-trione:

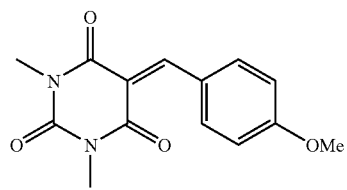

compounds of the benzylidenepyrazolone type, such as 4-(4-methoxybenzylidene)-5-methyl-2-phenyl-2,4-dihydropyrazol-3-one:

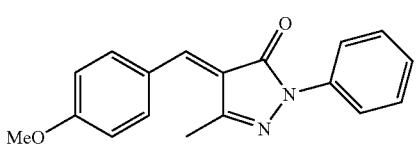

compounds of the benzylideneimidazolone type, such as 5-(4-methoxybenzylidene)-2-phenyl-3,5-dihydroimidazol-4-one:

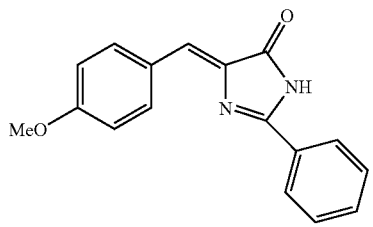

compounds of the chalcone type, such as 1-(2-hydroxy-4-methoxyphenyl)-3-phenylpropenone:

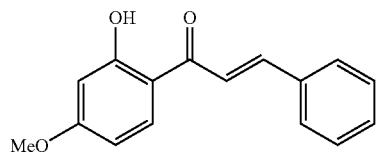

benzylidenone compounds as described in FR-2,506,156, for example 3-hydroxy-1-(2-hydroxy-4-methoxyphenyl)-3-phenylpropenone:

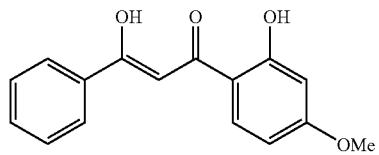

Mention may be made, as examples of compounds of formula (10) in which n'=2, which are insoluble, which screen out UV radiation and which have a mean particle size of between 10 nm and 5 μm, of the following families:

compounds of the phenylenebis(methylidenenorcamphor) type as described in EP-0-693,471, for example 1,4-phenylenebis{3-methylidenebicyclo[2.2.1]-heptan-2-one}:

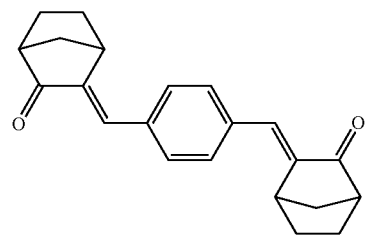

compounds of the phenylenebis(methylidenecamphor) type as described in FR-2-528,420, for example 1,4-phenylenebis{3-methylidene-1,7,7-trimethylbicyclo[2.2.1]heptan-2-one}:

1,3-phenylenebis{3-methylidene-1,7,7-trimethyl-bicyclo[2.2.1]heptan-2-one}:

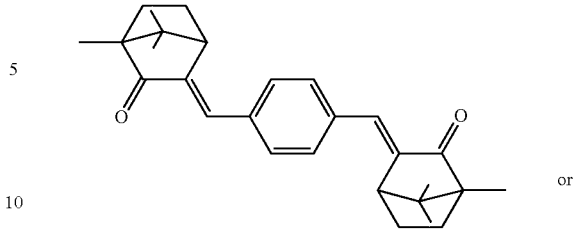

or

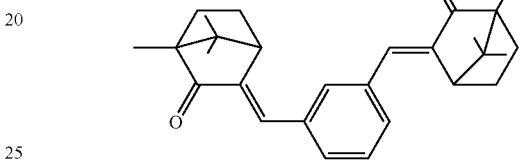

compounds of the phenylenebis(methylidenecamphorsulfonamide) type, such as those described in FR-2-529,887, for example 1,4-phenylene-bis{3,3'-methylidenecamphor-10,10'-ethylsulfonamide or -(2-ethylhexyl)sulfonamide}:

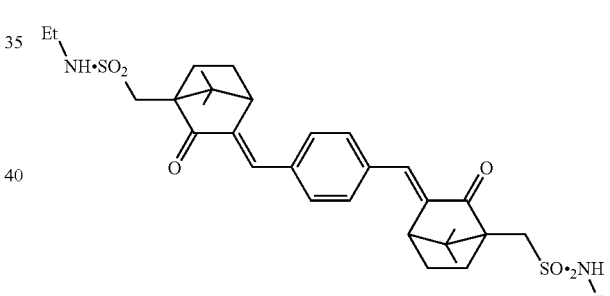

or

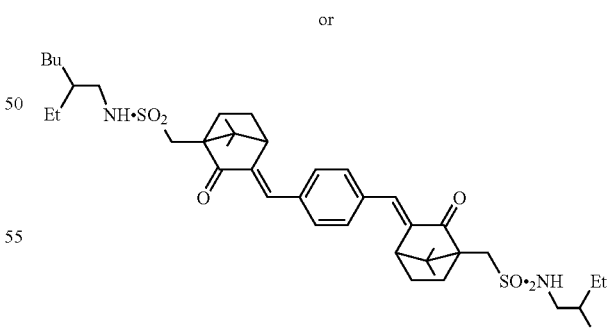

or compounds of the phenylenebis(methylidenecineole) type as described in the paper by E. Mariani et al., 16th IFSCC Congress, New York (1990), for example 1,4-phenylenebis{5-methylidene-3,3-dimethyl-2-oxa-bicyclo[2.2.2]octan-6-one}:

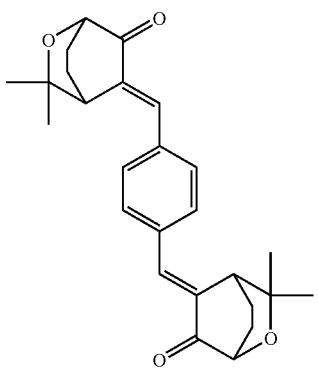

compounds of the phenylenebis(methylideneketo-tricyclodecane) type as described in EP-0-694,521, such as 1,4-phenylenebis(octahydro-4,7-methano-6-inden-5-one):

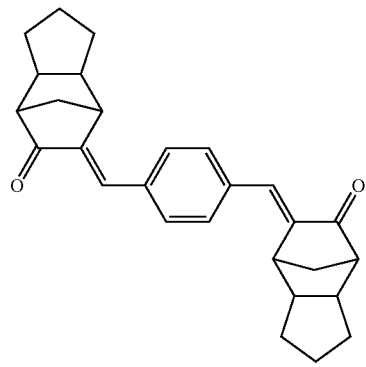

compounds of the phenylenebis(alkylene ketone) type, such as those described in JP 04 134 041, for example 1,4-phenylenebis(4,4-dimethylpent-1-en-3-one):

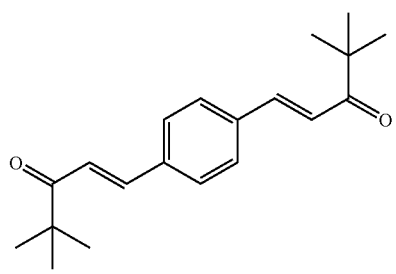

compounds of the phenylenebis(methylidenefuranone) type as described in FR-2-638,354, for example 1,4-phenylenebis(4-methylidene-2,2,5,5-tetramethyldihydrofuran-3one):

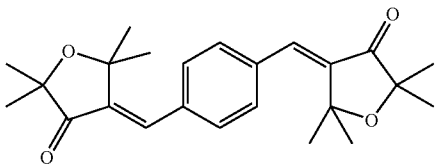

compounds of the phenylenebis(methylidene-quinuclidinone) type, such as those described in EP-0-714,880, for example 1,4-phenylene-bis{2-methylidene-1-azabicyclo[2.2.2]octan-3-one}:

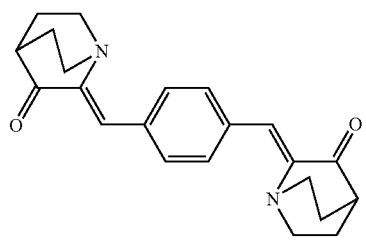

Mention may be made, as compounds of formula (11), of the following families:

compounds of the bis(benzylidene)cycloalkanone type, such as 2,5-di(benzylidene)cyclopentanone:

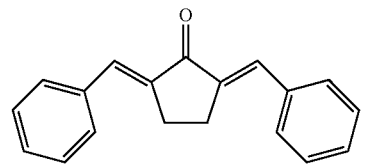

compounds of the γ-pyrone type as described in JP 04 290 882, for example 2,6-bis(3,4-dimethoxyphenyl)pyran-4-one:

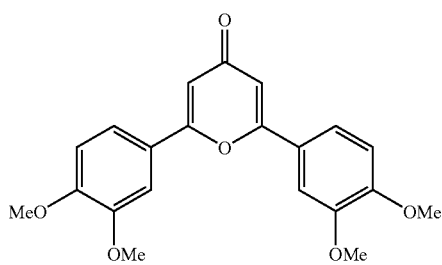

Preference is very particularly given, among these insoluble organic compounds which screen out UV radiation of the aryl vinylene ketone type, to the compounds of formula (10) in which n'=2.

Mention may be made, among insoluble organic screening agents of the phenylenebis(benzoxazinone) type, of those corresponding to the following formula (12):

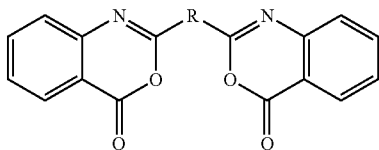

(12)

with R representing a divalent aromatic residue chosen from the following formulae (e″) to (h″):

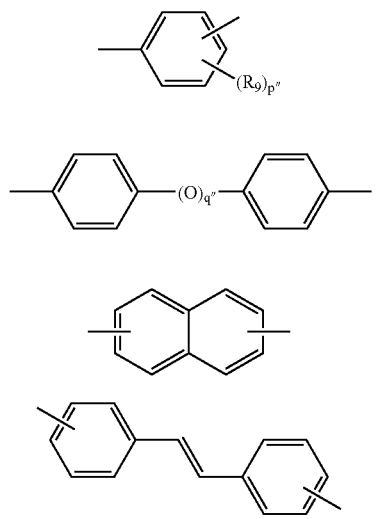

in which:
each of the $R_9$ symbols independently represents an OH group, a halogen atom, a linear or branched $C_{1-6}$ alkyl group optionally comprising a silicon atom, a linear or branched $C_{1-6}$ alkoxy group optionally comprising a silicon atom, a linear or branched $C_{1-5}$ alkoxycarbonyl group, or a linear or branched $C_{1-6}$ alkylsulfonamide group optionally comprising a silicon atom or an amino acid functional group,
p″ represents an integer between 0 and 4 inclusive,
q″ represents 0 or 1.

Mention may be made, as examples of compounds of formula (12), which are insoluble, which screen out UV radiation and which have a mean particle size of between 10 nm and 5 μm, of the following derivatives:

2,2′-p-phenylenebis(3,1-benzoxazin-4-one), commercial product Cyasorb UV-3638 from Cytec,
2,2′-(4,4′-biphenylene)bis(3,1-benzoxazin-4-one),
2,2′-(2,6-naphthylene)bis(3,1-benzoxazin-4-one).

Mention may be made, among insoluble organic screening agents of the acrylonitrile amide, sulfonamide or carbamate derivative type, of those corresponding to the following formula (13):

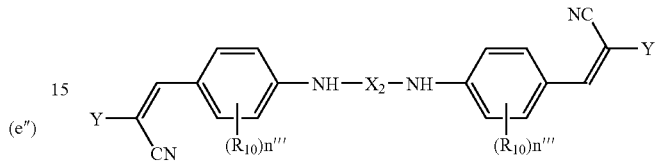

(13)

in which:
$R_{10}$ represents a linear or branched $C_{1-8}$ alkyl group,
n‴ has the value 0, 1 or 2,
$X_2$ represents a divalent radical of formula $-(C=O)-R_{11}-(C=O)-$, $-SO_2-R_{11}-SO_2-$ or $-(C=O)-O-R_{11}-O-(C=O)-$,
Y represents a $-(C=O)-R_{12}$ or $-SO_2R_{13}$ radical,
$R_{11}$ represents a single bond or a linear or branched, divalent $C_1-C_{30}$ alkylene or $C_3-C_{30}$ alkenylene radical which can carry one or more hydroxyl substituents and which can comprise, in the carbonaceous chain, one or more heteroatoms chosen from oxygen, nitrogen and silicon atoms,
$R_{12}$ represents an $-OR_{14}$ or $-NHR_{14}$ radical,
$R_{13}$ represents a linear or branched $C_1-C_{30}$ alkyl radical or a phenyl ring which is unsubstituted or substituted by $C_1-C_4$ alkyl or alkoxy radicals,
$R_{14}$ represents a linear or branched $C_1-C_{30}$ alkyl or $C_3-C_{30}$ alkenyl radical which can carry one or more hydroxyl substituents and which can comprise, in the carbonaceous chain, one or more heteroatoms chosen from oxygen, nitrogen and silicon atoms.

Although only the isomers in which the cyano substituent is in the cis position with respect to the para-aminophenyl substituent are represented in the above formula (13), this formula should be understood as also encompassing the corresponding trans isomers; for each of the two double bonds, and independently, the cyano and para-aminophenyl substituents can be in the cis or trans configuration with respect to one another.

Mention may be made, as example, of the dimer of 2-ethylhexyl 2-cyano-3-[4-(acetylamino)phenyl]-acrylate of formula:

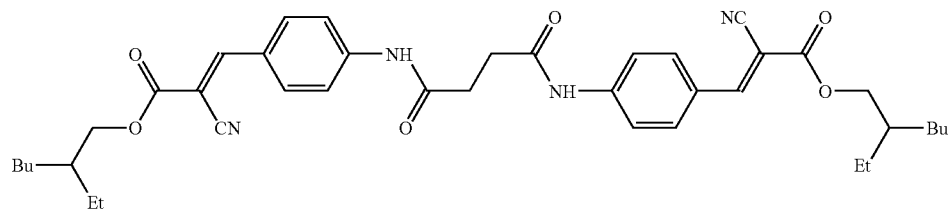

Another specific family of insoluble organic screening agents in accordance with the invention are the polyvalent metal salts (for example, $Ca^{2+}$, $Zn^{2+}$, $Mg^{2+}$, $Ba^{2+}$, $Al^{3+}$ or $Zr^{4+}$) of sulfonic or carboxylic organic screening agents, such as the polyvalent metal salts of sulfonated derivatives of benzylidenecamphor, such as those described in FR-A-2,639,347; the polyvalent metal salts of sulfonated derivatives of benzimidazole, such as those described in EP-A-893,119; or the polyvalent metal salts of cinnamic acid derivatives, such as those described in JP-87 166 517.

Mention may also be made of metal or ammonium or substituted ammonium complexes of UV-A and/or UV-B organic screening agents as described in WO 93/10753, WO 93/11095 and WO 95/05150.

The insoluble UV-screening agent or agents of the invention are present at a total concentration of between 0.5% and 15% by weight approximately and preferably between 1% and 10% by weight approximately and more particularly from 2% to 8% by weight with respect to the total weight of the composition.

The choice may be made, among preferred 4,4-diarylbutadiene compounds in accordance with the invention, of the compounds corresponding to the following formula (I):

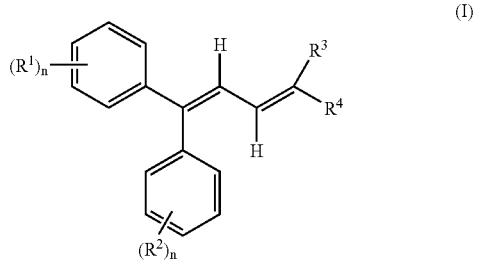

(I)

in which the diene system has the Z,Z; Z,E; E,Z or E,E configuration or is composed of mixtures of the said configurations, and where:

$R^1$ and $R^2$, which are identical or different, denote hydrogen; a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical; a linear or branched $C_1$–$C_{20}$ alkoxycarbonyl radical; a linear or branched $C_1$–$C_{12}$ monoalkylamino radical; a linear or branched di($C_1$–$C_{12}$)alkylamino radical; an aryl radical; a heteroaryl radical or a water-solubilizing substituent chosen from a carboxylate group, a sulfonate group or an ammonium residue;

$R^3$ denotes a $COOR^5$, $COR^5$, $CONR^5R^6$ or CN group; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; or a $C_3$–$C_7$ heteroaryl radical;

$R^4$ denotes a $COOR^6$, $COR^6$, $CONR^5R^6$ or CN group; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; or a heteroaryl radical;

$R^5$ and $R^6$, which are identical or different, denote hydrogen; $[V]_o$—$R^7$, $C_1$–$C_6$-alkylene-$SO_3U$; $C_1$–$C_6$-alkylene-$PO_3U$; $C_1$–$C_6$-alkylene-$N(R^8)_3{}^+B'^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; or a heteroaryl radical;

V denotes a —$CH_2$—$CH_2$—W—, —$CH_2CH_2CH_2W$—, —$CH(CH_3)$—$CH_2$—W—, —$CH_2$—$CH_2$—$CH_2$—$CH_2$—W— or —$CH_2$—$CH(CH_2CH_3)$—W— group;

B' denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R^8)_4{}^+$;

W denotes O or NH;

$R^7$ and $R^8$, which are identical or different, denote hydrogen; a linear or branched $C_1$–$C_6$ alkyl radical; a linear or branched $C_2$–$C_6$ alkenyl radical; or a linear or branched $C_1$–$C_6$ acyl radical;

$R^9$ denotes hydrogen; a linear or branched $C_1$–$C_6$ alkyl radical; or a $C_2$–$C_6$ alkenyl radical;

n varies from 1 to 3;

o varies from 0 to 150.

Mention may be made, as $C_1$–$C_{20}$ alkyl radicals, of, for example:

methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

Mention may be made, as $C_2$–$C_{10}$ alkenyl groups, of, for example: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethyl-butenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl or n-decenyl.

Mention may be made, as $C_1$–$C_{12}$ alkoxy radicals for the radicals $R^1$ and $R^2$, of:

methoxy, n-propoxy, 1-methylethoxy, 1-methylpropoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy or 2-ethylhexoxy.

Mention may be made, as $C_3$–$C_{10}$ cycloalkyl radicals for the radicals $R^6$ and $R^7$, of, for example:

cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Mention may be made, as $C_3$–$C_{10}$ cycloalkenyl radicals having one or more double bonds for the radicals $R^6$ and $R^7$, of:

cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals can comprise one or more substituents (preferably from 1 to 3) chosen, for example, from halogen, such as chlorine, fluorine or bromine; cyano; nitro; amino; $C_1$–$C_4$ alkylamino; di($C_1$–$C_4$)alkylamino; $C_1$–$C_4$ alkyl; $C_1$–$C_4$ alkoxy; or hydroxyl. They can also comprise from 1 to 3 heteroatoms, such as sulfur, oxygen or nitrogen, the free valencies of which can be satisfied by a hydrogen or a $C_1$–$C_4$ alkyl radical.

Mention may be made, as acyl radicals, of, for example, formyl, acetyl, propionyl or n-butyryl.

The bicycloalkyl or bicycloalkenyl groups are chosen, for example, from bicyclic terpenes, such as pinane, bornane, pinene or camphor or adamantane derivatives.

The aryl groups are preferably chosen from phenyl or naphthyl rings which can comprise one or more substituents (preferably from 1 to 3) chosen, for example, from halogen, such as chlorine, fluorine or bromine; cyano; nitro; amino; $C_1$–$C_4$ alkylamino; di($C_1$–$C_4$)alkylamino; $C_1$–$C_4$ alkyl; $C_1$–$C_4$ alkoxy; or hydroxyl. Preference is more particularly given to phenyl, methoxyphenyl and naphthyl.

The heteroaryl groups generally comprise one or more heteroatoms chosen from sulfur, oxygen or nitrogen.

The water-solublizing groups are, for example, carboxylate or sulfonate groups and more particularly their salts with physiologically acceptable cations, such as alkali metal salts or trialkylammonium salts, such as tri(hydroxyalkyl)-ammonium or 2-methylpropan-1-ol-2-ammonium salts. Mention may also be made of ammonium groups, such as alkylammoniums, and their salified forms with physiologically acceptable anions.

The preferred compounds of formula (I) are chosen from those of following formula (Ia):

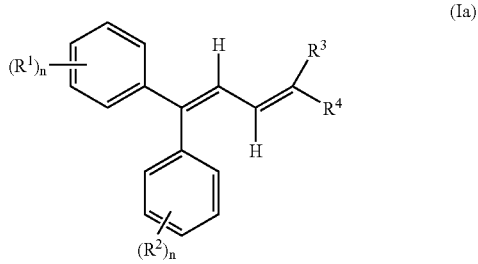

(Ia)

in which the diene system has the Z,Z; Z,E; E,Z or E,E configuration or is composed of mixtures of the said configurations, and where:
  $R^1$ and $R^2$, which are identical or different, denote hydrogen; a $C_1$–$C_8$ alkyl radical; a $C_1$–$C_8$ alkoxy radical; or a water-solubilizing substituent chosen from a carboxylate group, a sulfonate group or an ammonium residue;
  $R^3$ denotes a $COOR^5$, $CONR^5R^6$ or CN group;
  $R^4$ denotes a $COOR^6$ or $CONR^5R^6$ group;
  $R^5$ denotes hydrogen; $[V]_o$—$R^7$; $C_1$–$C_6$-alkylene-$SO_3U$; or $C_1$–$C_6$-alkylene-$N(R^8)_3{}^+B'^-$;
  $R^6$ denotes $[V]_o$—$R^7$; $C_1$–$C_6$-alkylene-$SO_3U$; or $C_1$–$C_6$-alkylene-$N(R^8)_3{}^+B'^-$;
  V denotes a —$CH_2$—$CH_2$—O—, —$CH_2CH_2CH_2O$— or —$CH(CH_3)$—$CH_2$—O— group;
  B' denotes Cl, Br, I or $SO_4R^9$;
  U denotes hydrogen, $Na^+$, $K^+$, $Mg^{2+}$, $Ca^{2+}$, $Li^+$, $Al^{3+}$ or —$N(R^8)_4{}^+$;
  $R^7$, $R^8$ and $R^9$, which are identical or different, denote hydrogen or a linear or branched $C_1$–$C_3$ alkyl radical;
  o varies from 0 to 50;
  n varies from 1 to 3.

The even more preferred compounds of formula (I) are chosen from those corresponding to the following formula (Ib):

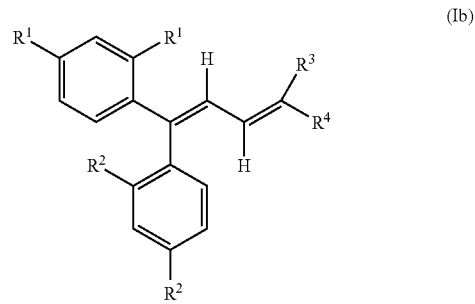

(Ib)

in which the diene system has the Z,Z; Z,E; E,Z or E,E configuration or is composed of mixtures of the said configurations, and where:
  $R^1$ and $R^2$, which are identical or different, denote hydrogen; a $C_1$–$C_8$ alkyl radical; or a $C_1$–$C_8$ alkoxy radical;
  $R^3$ denotes a $COOR^5$, $CONR^5R^6$ or CN group;
  $R^4$ denotes a $COOR^6$ or $CONR^5R^6$ group;
  $R^5$ denotes hydrogen; $[V]_o$—$R^7$; $C_1$–$C_6$-alkylene-$SO_3U$; or $C_1$–$C_6$-alkylene-$N(R^8)_3{}^+B'^-$;
  $R^6$ denotes $[V]_o$—$R^7$; $C_1$–$C_6$-alkylene-$SO_3U$; or $C_1$–$C_6$-alkylene-$N(R^8)_3{}^+B'^-$;
  V denotes a —$CH_2$—$CH_2$—O—, —$CH_2CH_2CH_2O$— or —$CH(CH_3)$—$CH_2$—O— group;
  B' denotes Cl, Br, I or $SO_4R^9$;
  U denotes hydrogen, $Na^+$, $K^+$, $Mg^{2+}$, $Ca^{2+}$, $Li^+$, $Al^{3+}$ or —$N(R^8)_4{}^+$;
  $R^7$, $R^8$ and $R^9$, which are identical or different, denote hydrogen or a linear or branched $C_1$–$C_3$ alkyl radical;
  o varies from 0 to 50.

The even more preferred compounds of formula (I) are chosen from those corresponding to the following formula (Ic):

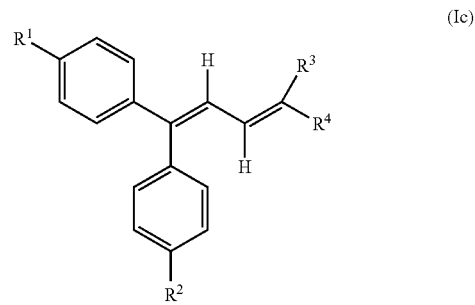

(Ic)

in which the diene system has the Z,Z; Z,E; E,Z or E,E configuration or is composed of mixtures of the said configurations, and where:
  $R^1$ and $R^2$, which are identical or different, denote hydrogen; a $C_1$–$C_8$ alkyl radical; or a $C_1$–$C_8$ alkoxy radical;
  $R^3$ denotes a $COOR^5$, $CONR^5R^6$ or CN group;
  $R^4$ denotes a $COOR^6$ or $CONR^5R^6$ group;

$R^5$ denotes hydrogen; $[V]_o$—$R^7$; $C_1$–$C_6$-alkylene-$SO_3U$; or $C_1$–$C_6$-alkylene-$N(R^8)_3{}^+B'^-$;

$R^6$ denotes $[V]_o$—$R^7$; $C_1$–$C_6$-alkylene-$SO_3U$; or $C_1$–$C_6$-alkylene-$N(R^8)_3{}^+B'^-$;

V denotes a —$CH_2$—$CH_2$—O—, —$CH_2CH_2CH_2O$— or —$CH(CH_3)$—$CH_2$—O— group;

B' denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R_8)_4{}^+$;

$R^7$, $R^8$ and $R^9$, which are identical or different, denote hydrogen or a linear or branched $C_1$–$C_3$ alkyl radical;

o varies from 0 to 50.

The even more particularly preferred compounds are chosen from the following compounds:

(I1)

(I2)

(I3)

(I4)

(I5)

The compounds of formula (I) as defined above are known per se and their structures and their syntheses are described in EP-0-967,200, DE-197,46,654 and DE-197,55,649 (which form an integral part of the content of the description).

Mention may also be made, among the preferred 4,4-diarylbutadiene compounds in accordance with the invention, of the oligomers corresponding to the following formula (II):

(II)

in which the diene system has the Z,Z; Z,E; E,Z or E,E configuration or is composed of mixtures of the said configurations, and where:

$R^1$, $R^2$, $R^3$ and n have the same meanings indicated in the preceding formula (I);

Y' denotes an —O— or —$NR^{10}$— group;

$R^{10}$ denotes hydrogen; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl; or a heteroaryl;

X' denotes a linear or branched, aliphatic or cyclo-aliphatic, polyol residue comprising from 2 to 10 hydroxyl groups and with a valency of q; it being possible for the carbonaceous chain of the said residue to be interrupted by one or more sulfur or oxygen atoms; one or more imine groups; or one or more $C_1$–$C_4$ alkylimine groups;

q varies from 2 to 10.

X' is a polyol residue comprising from 2 to 10 hydroxyl groups and in particular:

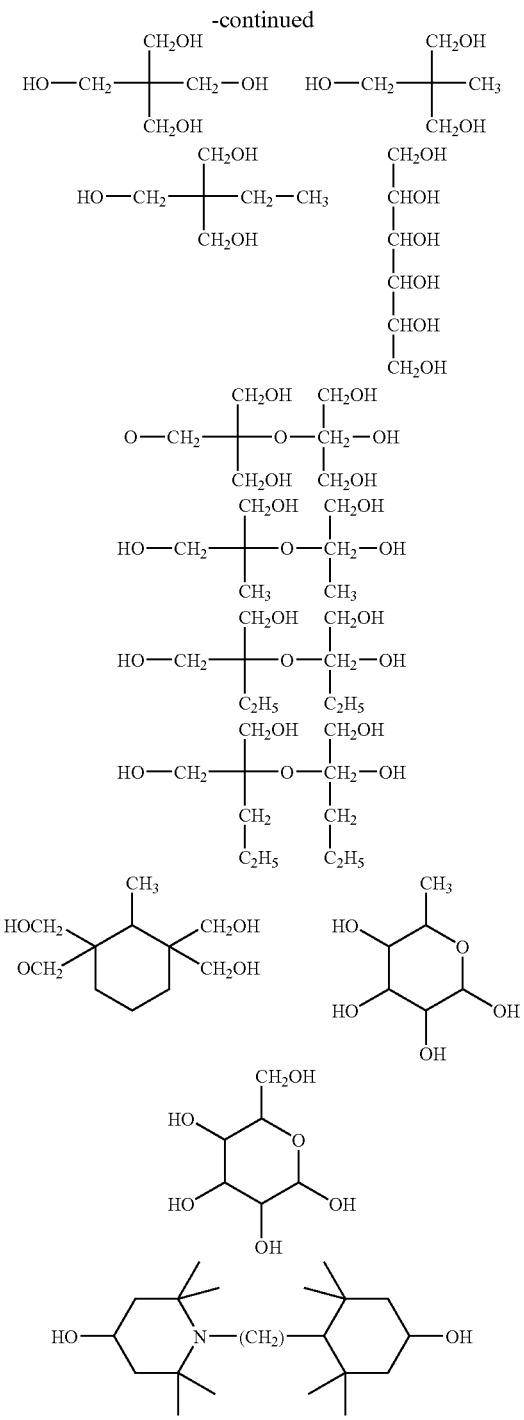

-continued

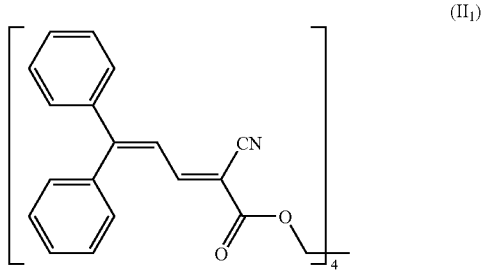

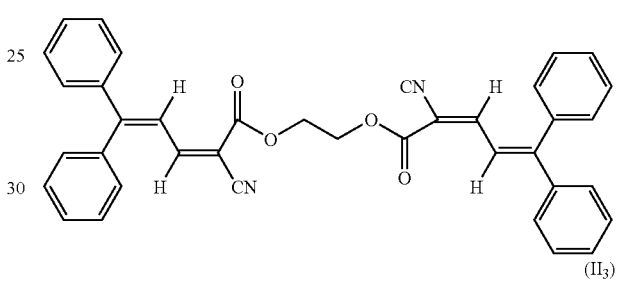

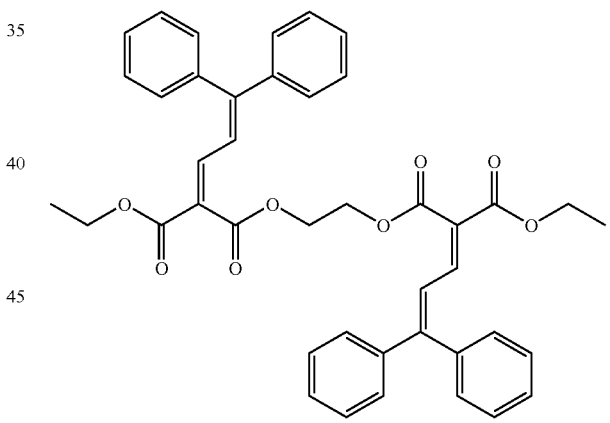

The most preferred compounds of formula (II) are those for which:

$R^1$ and $R^2$, which are identical or different, denote hydrogen; a $C_1$–$C_{12}$ alkyl radical; a $C_1$–$C_8$ alkoxy radical; or a water-solubilizing substituent chosen from a carboxylate group, a sulfonate group or an ammonium residue;

$R^3$ denotes a $COOR^5$, $CONR^5R^6$ or $CN$ group; a $C_3$–$C_{10}$ cyclo-alkyl radical; or a $C_7$–$C_{10}$ bicycloalkyl radical;

$R^5$ and $R^6$, which are identical or different, denote a linear or branched $C_1$–$C_{20}$ alkyl radical; a $C_3$–$C_{10}$ cyclo-alkyl radical; a $C_7$–$C_{10}$ bicycloalkyl radical; or optionally substituted naphthyl or phenyl;

X' denotes a polyol residue comprising from 2 to 6 hydroxyl groups and more particularly from 2 to 4.

The even more preferred compounds of formula (II) are those for which:

X' denotes an ethanol or pentaerythritol residue.

The even more particularly preferred compounds of formula (II) are chosen from the following compounds:

The compounds of formula (II) as defined above are known per se and their structures and their syntheses are described in EP-A-1,008,586 (which forms an integral part of the content of the description).

The 4,4-diarylbutadiene compounds in accordance with the invention are preferably present in the composition of the invention in proportions ranging from 0.5% to 15% by weight and more preferably from 1 to 10 and more preferably still from 2% to 8% by weight with respect to the total weight of the composition.

In addition, the compositions in accordance with the invention can comprise soluble organic UV-screening agents which are active in the UV-A and/or UV-B regions. They are chosen in particular from anthranilates; cinnamic derivatives; dibenzoylmethane derivatives; salicylic derivatives camphor derivatives; triazine derivatives, such as those described in U.S. Pat. No. 4,367,390, EP-863,145, EP-517,104, EP-570,838, EP-796,851, EP-775,698, EP-878,469 and EP-933,376; benzophenone derivatives; β,β-diphenylacrylate derivatives; benzotriazole derivatives; benzalmalonate derivatives; benzimidazole derivatives; imidazolines; bis-benzoazolyl derivatives as described in EP-669,323 and U.S. Pat. No. 2,463,264; p-aminobenzoic acid (PABA) derivatives; screening polymers and screening silicones, such as those described in particular in WO 93/04665; dimers derived from α-alkylstyrene, such as those described in DE-198,55,649; and their mixtures.

Mention may be made, as examples of additional soluble organic screening agents which are active in the UV-A and/or UV-B regions, of, denoted below under their INCI names:

para-Aminobenzoic Acid Derivatives:
PABA,
Ethyl PABA,
Ethyl Dihydroxypropyl PABA,
Ethylhexyl Dimethyl PABA, sold in particular under the name "Escalol 507" by ISP,
Glyceryl PABA,
PEG-25 PABA, sold under the name "Uvinul P25" by BASF,
Salicylic Derivatives:
Homosalate, sold under the name "Eusolex HMS" by Rona/EM Industries,
Ethylhexyl Salicylate, sold under the name "Neo Heliopan OS" by Haarmann and Reimer,
Dipropyleneglycol Salicylate, sold under the name "Dipsal" by Scher,
TEA Salicylate, sold under the name "Neo Heliopan TS" by Haarmann and Reimer,
Dibenzoylmethane Derivatives:
Butyl Methoxydibenzoylmethane, sold in particular under the trade name "Parsol 1789" by Hoffmann-LaRoche,
Isopropyl Dibenzoylmethane,
Cinnamic Derivatives:
Ethylhexyl Methoxycinnamate, sold in particular under the trade name "Parsol MCX" by Hoffmann-LaRoche,
Isopropyl Methoxy cinnamate,
Isoamyl Methoxy cinnamate, sold under the trade name "Neo Heliopan E 1000" by Haarmann and Reimer,
Cinoxate,
DEA Methoxycinnamate,
Diisopropyl Methylcinnamate,
Glyceryl Ethylhexanoate Dimethoxycinnamate,
β,β-Diphenylacrylate Derivatives:
Octocrylene, sold in particular under the trademark "Uvinul N539" by BASF,
Etocrylene, sold in particular under the trademark "Uvinul N35" by BASF,
Benzophenone Derivatives:
Benzophenone-1, sold under the trademark "Uvinul 400" by BASF,
Benzophenone-2, sold under the trademark "Uvinul D50" by BASF,
Benzophenone-3 or Oxybenzone, sold under the trademark "Uvinul M40" by BASF,
Benzophenone-4, sold under the trademark "Uvinul MS40" by BASF,
Benzophenone-5,
Benzophenone-6, sold under the trademark "Helisorb 11" by Norquay,
Benzophenone-8, sold under the trademark "Spectra-Sorb UV-24" by American Cyanamid,
Benzophenone-9, sold under the trademark "Uvinul DS-49" by BASF,
Benzophenone-12,
Benzylidenecamphor Derivatives:
3-Benzylidene camphor, manufactured under the name "Mexoryl SD" by Chimex,
4-Methylbenzylidene camphor, sold under the name "Eusolex 6300" by Merck,
Benzylidene Camphor Sulfonic Acid, manufactured under the name "Mexoryl SL" by Chimex,
Camphor Benzalkonium Methosulfate, manufactured under the name "Mexoryl SO" by Chimex,
Terephthalylidene Dicamphor Sulfonic Acid, manufactured under the name "Mexoryl SX" by Chimex,
Polyacrylamidomethyl Benzylidene Camphor, manufactured under the name "Mexoryl SW" by Chimex,
Phenylbenzimidazole Derivatives:
Phenylbenzimidazole Sulfonic Acid, sold in particular under the trademark "Eusolex 232" by Merck,
Disodium Phenyl Dibenzimidazole Tetrasulfonate, sold under the trademark "Neo Heliopan AP" by Haarmann and Reimer,
Triazine Derivatives:
Anisotriazine, sold under the trademark "Tinosorb S" by Ciba-Geigy,
Ethylhexyl triazone, sold in particular under the trademark "Uvinul T150" by BASF,
Diethylhexyl Butamido Triazone, sold under the trademark "Uvasorb HEB" by Sigma 3V,
Benzotriazole Derivatives:
Drometrizole Trisiloxane, sold under the name "Silatrizole" by Rhodia Chimie,
Anthranilic Derivatives:
Menthyl anthranilate, sold under the trademark "Neo Heliopan MA" by Haarmann and Reimer,
Imidazoline Derivatives:
Ethylhexyl Dimethoxybenzylidene Dioxoimidazoline Propionate,
Benzalmalonate Derivatives:
Polyorganosiloxane comprising a benzalmalonate functional group, sold under the trademark "Parsol SLX" by Hoffmann-LaRoche, and their mixtures.

The additional soluble organic UV-screening agents which are more particularly preferred are chosen from the following compounds:
Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic Acid,
Benzophenone-3,
Benzophenone-4,
Benzophenone-5,
4-Methylbenzylidene camphor,
Disodium Phenyl Dibenzimidazole Tetrasulfonate,
Anisotriazine,
Ethylhexyl triazone,
Diethylhexyl Butamido Triazone,
Drometrizole Trisiloxane, and their mixtures.

The additional soluble UV-screening agent or agents are generally present in concentrations ranging from 0.15% to 15% by weight approximately, and preferably from 1% to 10% by weight approximately, with respect to the total weight of the composition.

The compositions according to the invention can also comprise agents for the artificial tanning and/or browning of the skin (self-tanning agents), such as, for example, dihydroxyacetone (DHA).

The compositions of the invention can additionally comprise conventional cosmetic adjuvants chosen in particular from fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, colorants or any other ingredient commonly used in cosmetics, in particular for the manufacture of antisun compositions in the form of emulsions.

The fatty substances can be composed of an oil or a wax or their mixtures. The term "oil" is understood to mean a compound which is liquid at ambient temperature. The term "wax" is understood to mean a compound which is solid or substantially solid at ambient temperature and for which the melting point is generally greater than 35° C. They also comprise fatty acids, fatty alcohols and esters of fatty acids which are linear or cyclic, such as derivatives of benzoic acid, trimellitic acid and hydroxybenzoic acid.

Mention may be made, as oils, of mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$–$C_{15}$ alkyl benzoate sold under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; or polyalkylenes.

Mention may be made, as waxy compounds, of paraffin wax, carnauba wax, beeswax or hydrogenated castor oil.

Mention may be made, among organic solvents, of lower alcohols and polyols.

Of course, a person skilled in the art will take care to choose this or these optional additional compounds and/or their amounts so that the advantageous properties, in particular the synergistic effect, intrinsically attached to the compositions in accordance with the invention are not, or not substantially, detrimentally affected by the envisaged addition or additions.

The compositions of the invention can be prepared according to techniques well known to a person skilled in the art, in particular those intended for the preparation of emulsions of oil-in-water or water-in- oil type.

These compositions can be provided in particular in the form of a simple or complex emulsion (O/W, W/O, O/W/O or W/O/W), such as a cream, a milk, a gel or a cream gel, of a powder or of a solid tube and can optionally be packaged as an aerosol and provided in the form of a foam or spray.

When it is a question of an emulsion, the aqueous phase of the latter can comprise a nonionic vesicular dispersion prepared according to known processes (Bangham, Standish and Watkins, J. Mol. Biol., 13, 238 (1965), FR-2-315,991 and FR-2-416,008). The cosmetic composition of the invention can be used as a composition for protecting the human epidermis or the hair against ultraviolet rays, as an antisun composition or as a makeup product.

When the cosmetic composition according to the invention is used in a regime or regimen for the protection of the human epidermis against UV rays or as an antisun composition, it can be provided in the form of a suspension or dispersion in solvents or fatty substances, in the form of a nonionic vesicular dispersion or in the form of an emulsion, preferably of oil-in-water type, such as a cream or a milk, in the form of an ointment, gel, cream gel, solid tube, powder, stick, aerosol foam or spray.

When the cosmetic composition according to the invention is used for the protection of the hair against UV rays, it can be provided in the form of a shampoo, lotion, gel, emulsion or nonionic vesicular dispersion and can constitute, for example, a rinse-out composition, to be applied before or after shampooing, before or after dyeing or bleaching, and before, during or after perming or hair straightening, a styling or treating lotion or a styling or treating gel, a lotion or a gel for blow-drying or hair setting, or a composition for perming or straightening, dyeing or bleaching the hair.

When the composition is used as a product for making up the eyelashes, eyebrows or skin, such as a treatment cream for the epidermis, foundation, lipstick tube, eyeshadow, face powder, mascara or eyeliner, it can be provided in the anhydrous or aqueous, pasty or solid form, such as oil-in-water or water-in-oil emulsions, nonionic vesicular dispersions, or suspensions.

By way of indication, for the antisun formulations in accordance with the invention which exhibit a vehicle of oil-in-water emulsion type, the aqueous phase (comprising in particular the hydrophilic screening agents) generally represents from 50% to 95% by weight, preferably from 70% to 90% by weight, with respect to the entire formulation, the oily phase (comprising in particular the lipophilic screening agents) from 5% to 50% by weight, preferably from 10% to 30% by weight, with respect to the entire formulation, and the (co)emulsifier(s) from 0.5% to 20% by weight, preferably from 2% to 10% by weight, with respect to the entire formulation.

As indicated above, the present invention features the use of a composition according to the invention in the manufacture of cosmetic compositions for the protection of the skin and/or hair against ultraviolet radiation, in particular solar radiation.

The present invention also features the use of an amphiphilic polymer as defined above in the manufacture of a photoprotective cosmetic or dermatological composition comprising at least one organic UV-screening agent which is insoluble in the said emulsion, for the purpose of increasing the resistance to water of its screening power (persistence to water).

In order to further illustrate the present invention and the advantages thereof, the following specific examples are given, it being understood that same are intended only as illustrative and in nowise limitative.

In said examples to follow, all parts and percentages are given by weight, unless otherwise indicated.

The following Examples 1–5 illustrate specific compositions according to the invention.

TABLE 1

| COMPOSITION | EXAMPLE 1 |
| --- | --- |
| Glycerol mono/distearate/polyethylene glycol (100 EO) stearate mixture (Arlacel 165 FL, ICI) | 2 |
| Stearyl alcohol (Lanette 18, Henkel) | 1 |
| Palm oil stearic acid (Stéarine TP, Stéarinerie Dubois) | 2.5 |
| Polydimethylsiloxane (Dow Corning 200 Fluid, Dow Corning) | 0.5 |

TABLE 1-continued

| COMPOSITION | EXAMPLE 1 |
|---|---|
| $C_{12}/C_{15}$ Alkyl benzoate (Witconol TN, Witco) | 20 |
| Triethanolamine | 0.5 |
| Methylene bis-benzotriazolyl tetramethylbutyl-phenol, in the form of an aqueous dispersion (Tinosorb M, Ciba Specialty Chemicals) | 5 |
| Compound of formula (10) | 8 |
| Glycerol | 4 |
| Triethanolamine | 0.3 |
| Polyacrylic acid (Synthalen K, 3V) | 0.4 |
| Preservatives | q.s |
| Demineralized water q.s. for | 100 g |

TABLE 2

| COMPOSITION | EXAMPLE 2 |
|---|---|
| 80/20 Mixture of cetearyl alcohol and of oxyethylenated (33 EO) cetearyl alcohol (Sinnowax AO, Henkel) | 7 |
| Mixture of glycerol mono- and distearate (Cerasynt SD-V, ISP) | 2 |
| Cetyl alcohol | 1.5 |
| Polydimethylsiloxane (Dow Corning 200 Fluid, Dow Corning) | 1.5 |
| Liquid petrolatum | 15 |
| Methylene bis-benzotriazolyl tetramethylbutyl-phenol, in the form of an aqueous dispersion (Tinosorb M, Ciba Specialty Chemicals) | 3 |
| Compound of formula (11) | 6 |
| Titanium dioxide (MT100T, Tayca) | 15 |
| Glycerol | 15 |
| Preservatives | q.s. |
| Demineralized water q.s. for | 100 g |

TABLE 3

| COMPOSITION | EXAMPLE 3 |
|---|---|
| Glycerol mono/distearate/polyethylene glycol (100 EO) stearate mixture (Arlacel 165 FL, ICI) | 2 |
| Stearyl alcohol (Lanette 18, Henkel) | 1 |
| Palm oil stearic acid (Stéarine TP, Stéarinerie Dubois) | 2.5 |
| Polydimethylsiloxane (Dow Corning 200 Fluid, Dow Corning) | 0.5 |
| $C_{12}/C_{15}$ Alkyl benzoate (Witconol TN, Witco) | 20 |
| Triethanolamine | 0.5 |
| Methylene bis-benzotriazolyl tetramethylbutyl-phenol, in the form of an aqueous dispersion (Tinosorb M, Ciba Specialty Chemicals) | 5 |
| Compound of formula (13) | 8 |
| Glycerol | 4 |
| Triethanolamine | 0.3 |
| Polyacrylic acid (Synthalen K, 3V) | 0.4 |
| Preservatives | q.s |
| Demineralized water q.s. for | 100 g |

TABLE 4

| COMPOSITION | EXAMPLE 4 |
|---|---|
| 80/20 Mixture of cetearyl alcohol and of oxyethylenated (33 EO) cetearyl alcohol (Sinnowax AO, Henkel) | 7 |
| Mixture of glycerol mono- and distearate (Cerasynt SD-V, ISP) | 2 |
| Cetyl alcohol | 1.5 |
| Polydimethylsiloxane (Dow Corning 200 Fluid, Dow Corning) | 1.5 |
| Liquid petrolatum | 15 |
| Methylene bis-benzotriazolyl tetramethylbutyl-phenol, in the form of an aqueous dispersion (Tinosorb M, Ciba Specialty Chemicals) | 3 |
| Compound of formula (15) | 6 |
| Ethylhexyl Methoxycinnamate (Parsol MCX, Hoffmann-LaRoche) | 7 |
| Glycerol | 15 |
| Preservatives | q.s. |
| Demineralized water q.s. for | 100 g |

TABLE 5

| COMPOSITION | EXAMPLE 5 |
|---|---|
| Glycerol mono/distearate/polyethylene glycol (100 EO) stearate mixture (Arlacel 165 FL, ICI) | 2 |
| Stearyl alcohol (Lanette 18, Henkel) | 1 |
| Palm oil stearic acid (Stéarine TP, Stéarinerie Dubois) | 2.5 |
| Polydimethylsiloxane (Dow Corning 200 Fluid, Dow Corning) | 0.5 |
| $C_{12}/C_{15}$ Alkyl benzoate (Witconol TN, Witco) | 20 |
| Triethanolamine | 0.5 |
| Methylene bis-benzotriazolyl tetramethylbutyl-phenol, in the form of an aqueous dispersion (Tinosorb M, Ciba Specialty Chemicals) | 5 |
| Compound of formula (16) | 8 |
| Glycerol | 4 |
| Triethanolamine | 0.3 |
| Polyacrylic acid (Synthalen K, 3V) | 0.4 |
| Preservatives | q.s |
| Demineralized water q.s. for | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological UV-screening composition, suited for the photoprotection of the skin and/or hair, comprising:
    (a) particulates of at least one insoluble organic UV-screening agent having a particle size ranging from 10 nm to 5 μm, as a first screening agent, and
    (b) at least one 4,4-diarylbutadiene compound, as a second UV-screening agent, formulated into a topically applicable, cosmetically/dermatologically acceptable vehicle therefor.

2. The cosmetic/dermatological UV-screening composition as defined by claim 1, said first and said second UV-screening agents being present therein in a proportion producing a synergistic activity with regard to the sun protection factors conferred.

3. The cosmetic/dermatological UV-screening composition as defined by claim 1, said at least one insoluble organic UV-screening agent comprising an oxalanilide compound, a triazine compound, a benzotriazole compound, a vinyl amide compound, a cinnamamide compound, a benzazole and/or benzofuran and/or benzothiophene and/or indole compound, an aryl vinylene ketone compound, a phenylenebis(benzoxazinone) compound, an acrylonitrile amide, sulfonamide or carbamate compound, or mixture thereof.

4. The cosmetic/dermatological UV-screening composition as defined by claim 3, comprising at least one oxalanilide compound UV-screening agent having the formula (1):

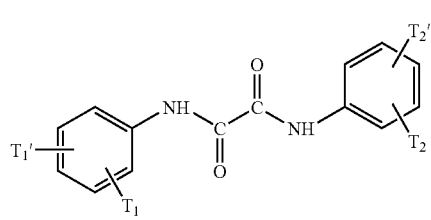

in which $T_1$, $T'_1$, $T_2$ and $T'_2$, which may be identical or different, are each a $C_1$–$C_8$ alkyl radical or a $C_1$–$C_8$ alkoxy radical.

5. The cosmetic/dermatological UV-screening composition as defined by claim 4, comprising an oxalanilide compound UV-screening agent having at least one of the following formulae:

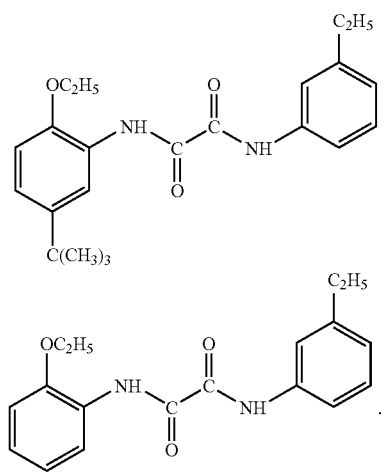

6. The cosmetic/dermatological UV-screening composition as defined by claim 3, comprising at least one triazine compound UV-screening agent having the formula (2):

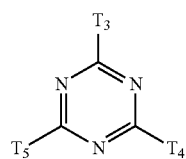

in which $T_3$, $T_4$ and $T_5$ are independently phenyl, phenoxy or pyrrolo, in which the phenyl, phenoxy and pyrrolo groups are optionally substituted by one, two or three substituents selected from among OH, $C_1$–$C_{18}$ alkyl or alkoxy, $C_1$–$C_{18}$ carboxyalkyl, $C_5$–$C_8$ cycloalkyl, a methylbenzylidenecamphor group, a —(CH=CH)$_n$(CO)—OT$_6$ group, wherein $T_6$ is either $C_1$–$C_{18}$ alkyl or cinnamyl, and n has the value 0 or 1.

7. The cosmetic/dermatological UV-screening composition as defined by claim 3, said at least one triazine compound UV-screening agent comprising an insoluble s-triazine derivative bearing benzalmalonate and/or phenylcyanoacrylate substituents.

8. The cosmetic/dermatological UV-screening composition as defined by claim 7, said triazine compound UV-screening agent comprising:

2,4,6-tris(diethyl 4'-aminobenzalmalonate)-s-triazine, 2,4,6-tris(diisopropyl 4'-aminobenzalmalonate)-s-triazine, 2,4,6-tris(dimethyl 4'-aminobenzalmalonate)-s-triazine, 2,4,6-tris(ethyl α-cyano-4-aminocinnamate)-s-triazine or mixture thereof.

9. The cosmetic/dermatological UV-screening composition as defined by claim 3, said at least one triazine compound UV-screening agent comprising an insoluble s-triazine derivative bearing benzotriazole and/or benzothiazole substituents.

10. The cosmetic/dermatological UV-screening composition as defined by claim 9, said triazine compound UV-screening agent comprising:

2,4,6-tris[(3'-(benzotriazol-2-yl)-2'-hydroxy-5'-methyl) phenylamino]-s-triazine, 2,4,6-tris[(3'-(benzotriazol-2-yl)-2'-hydroxy-5'-tert-octyl) phenylamino]-s-triazine, or mixture thereof.

11. The cosmetic/dermatological UV-screening composition as defined by claim 3, said at least one benzotriazole compound UV-screening agent having the following formula (3):

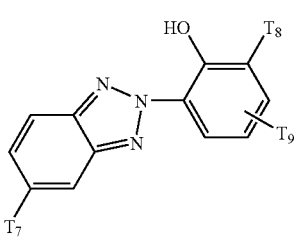

in which $T_7$ is a hydrogen atom or a $C_1$–$C_{18}$ alkyl radical; and the radicals $T_8$ and $T_9$, which may be identical or different, are each a $C_1$–$C_{18}$ alkyl radical optionally substituted by a phenyl radical.

12. The cosmetic/dermatological UV-screening composition as defined by claim 11, said at least one compound of formula (3) being selected from among the following compounds:

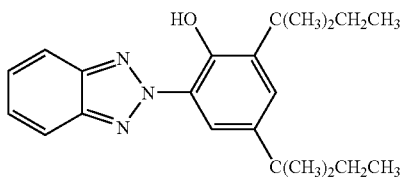

-continued

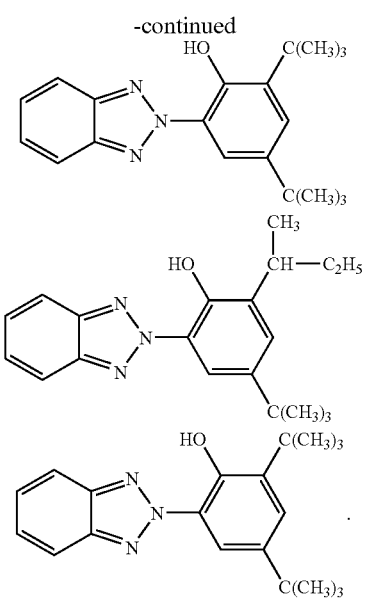

13. The cosmetic/dermatological UV-screening composition as defined by claim 3, said at least one insoluble UV-screening agent comprising [2,4'-dihydroxy-3-(2H-benzotriazol-2-yl)-5-(1,1,3,3-tetramethylbutyl)-2'-(n-octoxy)-5'-benzoyl]diphenylmethane having the following formula:

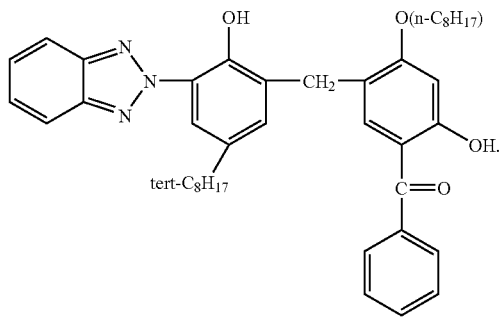

14. The cosmetic/dermatological UV-screening composition as defined by claim 3, comprising at least one methylenebis(hydroxyphenylbenzo-triazole) compound UV-screening agent having the following formula (4):

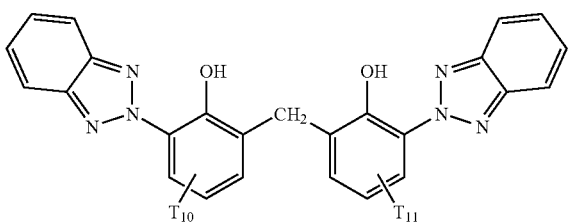

in which the $T_{10}$ and $T_{11}$ radicals, which may be identical or different, are each a $C_1$–$C_{18}$ alkyl radical optionally substituted by one or more radicals selected from among a $C_1$–$C_4$ alkyl radical, a $C_5$–$C_{12}$ cycloalkyl radical, or an aryl radical.

15. The cosmetic/dermatological UV-screening composition as defined by claim 14, said at least one compound of formula (4) comprising compounds having the following formulae of compound (a), compound (b), and/or compound (c):

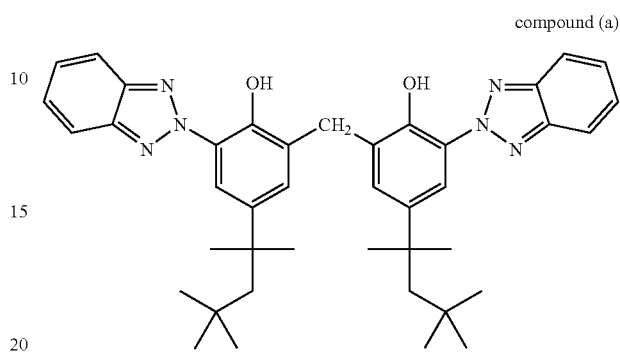

compound (a)

compound (b)

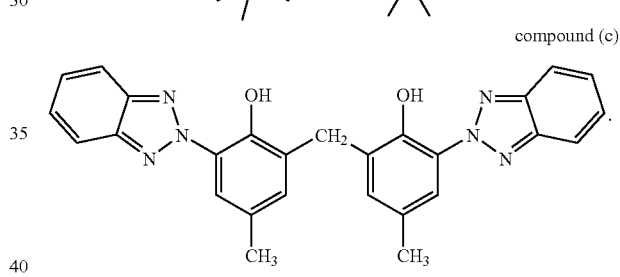

compound (c)

16. The cosmetic/dermatological UV-screening composition as defined by claim 3, comprising at least one vinyl amide compound UV-screening agent having the following formula (5):

$$T_{12}-(Y)_r-C(=O)-C(T_{13})=C(T_{14})-N(T_{15})(T_{16}) \qquad (5)$$

in which $T_{12}$ is a $C_1$–$C_{18}$ alkyl radical or a phenyl group optionally substituted by one, two or three radicals selected from among OH, a $C_1$–$C_{18}$ alkyl radical, a $C_1$–$C_8$ alkoxy radical, or a group —C(=O)—OT$_{17}$ wherein $T_{17}$ is a $C_1$–$C_{18}$ alkyl radical; and the radicals $T_{13}$, $T_{14}$, $T_{15}$ and $T_{16}$, which may be identical or different, are each a $C_1$–$C_{18}$ alkyl radical or a hydrogen atom; Y is N or O and r has the value 0 or 1.

17. The cosmetic/dermatological UV-screening composition as defined by claim 16, said at least one compound of formula (5) comprising:
 4-octylamino-3-penten-2-one;
 ethyl 3-octylamino-3-butenoate;
 3-octylamino-1-phenyl-2-buten-1-one;
 3-dodecylamino-1-phenyl-2-buten-1-one or mixtures thereof.

18. The cosmetic/dermatological UV-screening composition as defined by claim 3, comprising at least one cinnamamide compound UV-screening agent having the following formula (6):

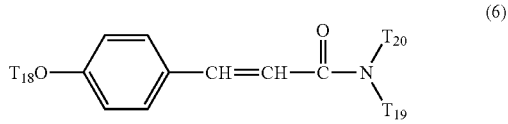

(6)

in which $OT_{18}$ is a hydroxyl or $C_1$–$C_4$ alkoxy radical; $T_{19}$ is hydrogen or $C_1$–$C_4$ alkyl; $T_{20}$ is a —(CONH)s-phenyl group where s has the value 0 or 1 and the phenyl group is optionally substituted by one, two or three groups selected from among OH, $C_1$–$C_{18}$ alkyl, $C_1$–$C_8$ alkoxy, or a —C(=O)—$OT_{21}$ group wherein $T_{21}$ is a $C_1$–$C_{18}$ alkyl radical.

19. The cosmetic/dermatological UV-screening composition as defined by claim 3, comprising at least one cinnamamide dimer UV-screening agent.

20. The cosmetic/dermatological UV-screening composition as defined by claim 19, comprising at least one insoluble UV-screening agent having the formula:

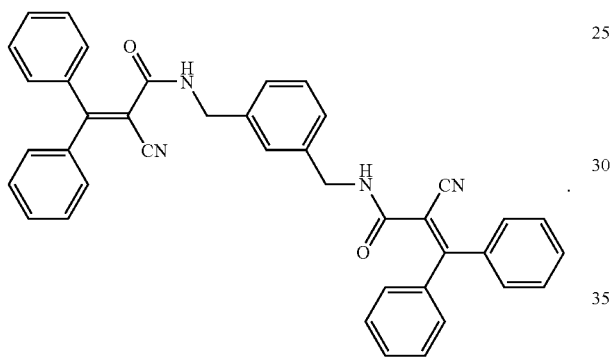

21. The cosmetic/dermatological UV-screening composition as defined by claim 3, comprising at least one benzazole compound UV-screening agent having one of the following formulae (7), (8) and (9):

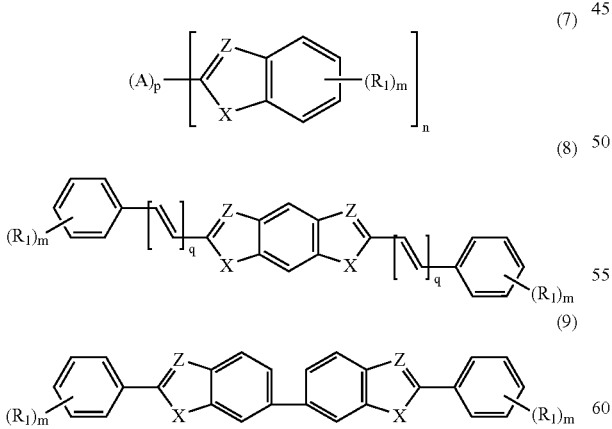

in which each of the X symbols independently represents an oxygen or sulfur atom or an $NR_2$ group, each of the Z symbols independently represents a nitrogen atom or a CH group, each of the $R_1$ symbols independently represents an OH group, a halogen atom, a linear or branched $C_1$–$C_{18}$ alkyl radical, optionally comprising a silicon atom, or a linear or branched $C_1$–$C_{18}$ alkoxy radical, each of the numbers m independently has the value 0, 1 or 2, n represents an integer between 1 and 4, inclusive, p is equal to 0 or 1, each of the numbers q is independently equal to 0 or 1, each of the $R_2$ symbols independently represents a hydrogen atom or a benzyl or linear or branched $C_1$–$C_{18}$ alkyl radical, optionally comprising a silicon atom, A represents a radical with a valency n selected from among those of the following formulae:

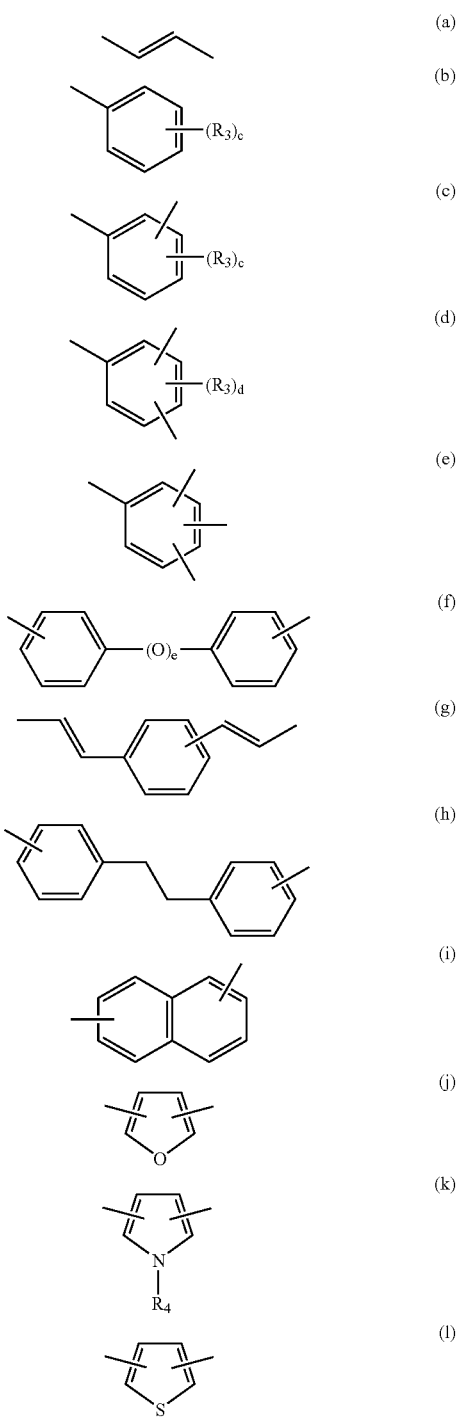

-continued (m)

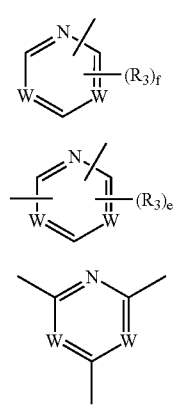

(n)

(o)

in which each of the R₃ symbols independently represents a halogen atom or a linear or branched $C_1$–$C_4$ alkyl or alkoxy radical or a hydroxyl group, $R_4$ represents a hydrogen atom or a linear or branched $C_1$–$C_4$ alkyl radical, c=0–4, d=0–3, e=0 or 1 and f=0–2.

22. The cosmetic/dermatological UV-screening composition as defined by claim 21, comprising at least one benzazole UV-screening compound of formula (7) selected from among 2-(benzoxazol-2-yl)-4-methylphenol, 2-(1H-benzimidazol-2-yl)-4-methoxyphenol or 2-(benzothiazol-2-yl) phenol, 2,2'-bisbenzimidazole, 5,5',6,6'-tetramethyl-2,2'-bisbenzimidazole, 5,5'-dimethyl-2,2'-bisbenzimidazole, 6-methoxy-2,2'-bisbenzimidazole, 2-(1H-benzimidazol-0.77 2-yl)benzothiazole, 2-(1H-benzimidazol-2-yl)benzoxazole and N,N'-dimethyl-2,2'-bisbenzimidazole, 1,4-phenylene-bis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenebis-(benzimidazolyl), 1,4-phenylenebis(N-(2-ethylhexyl)-2-benzimidazolyl) and 1,4-phenylenebis(N-trimethyl-silylmethyl-2-benzimidazolyl), 2-(2-benzofuranyl)-benzoxazole, 2-(benzofuranyl)-5-methylbenzoxazole and 2-(3-methyl-2-benzofuranyl)benzoxazole, and mixture thereof.

23. The cosmetic/dermatological UV-screening composition as defined by claim 21, comprising at least one benzazole UV-screening compound of formula (8) selected from among 2,6-diphenyl-1,7-dihydrobenzo[1,2-d;4,5-d']diimidazole, 2,6-distyryl-1,7-dihydrobenzo[1,2-d;4,5-d']diimidazole or 2,6-di(p-tert-butylstyryl)-1,7-dihydrobenzo[1,2-d;4,5-d']diimidazole and mixtures thereof.

24. The cosmetic/dermatological UV-screening composition as defined by claim 21, comprising the benzazole UV-screening compound of formula (9), 5,5'-bis(2-phenyl-benzimidazole).

25. The cosmetic/dermatological UV-screening composition as defined by claim 21, comprising at least one benzazole UV-screening compound selected from among 2-(1H-benzimidazol-2-yl)benzoxazole, 6-methoxy-2,2'-bisbenzimidazole, 2-(1H-benzimidazol-2-yl)benzothiazole, 1,4-phenylenebis(2-benzoxazolyl), 1,4-phenylenebis(2-benzimidazolyl), 1,3-phenylene-bis(2-benzoxazolyl), 1,2-phenylenebis(2-benzoxazolyl), 1,2-phenylenebis(2-benzimidazolyl) and 1,4-phenylene-bis(N-trimethylsilylmethyl-2-benzimidazolyl), or mixtures thereof.

26. The cosmetic/dermatological UV-screening composition as defined by claim 3, comprising at least one aryl vinylene ketone UV-screening compound having either of the following formulae (10) and (11):

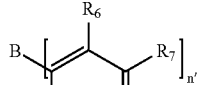

(10)

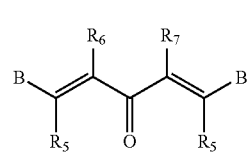

(11)

in which n'=1 or 2, B, in the formula (10) when n'=1 or in the formula (11), is an aryl radical selected from the following formulae (a') to (d') or, in the formula (10) when n'=2, is a radical selected from among the following formulae (e') to (h'):

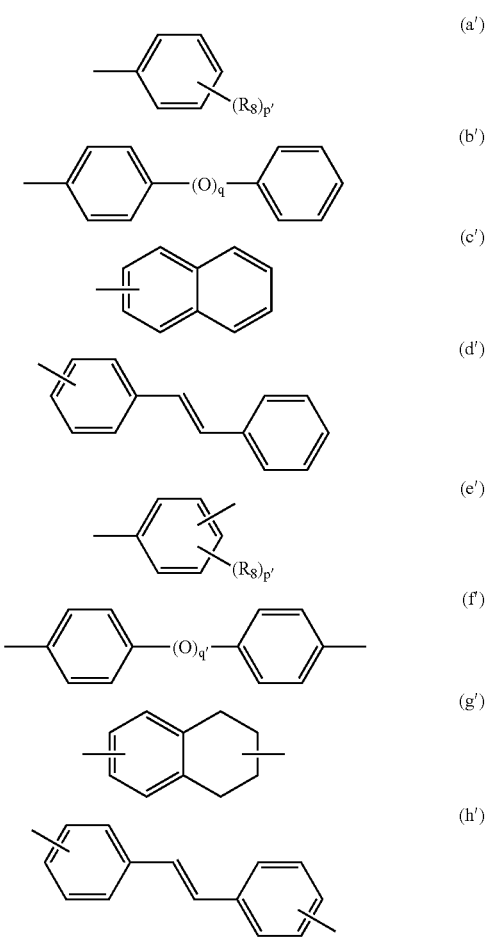

in which each of the $R_8$ symbols independently represents an OH group, a halogen atom, a linear or branched $C_1$–$C_6$ alkyl radical optionally comprising a silicon atom, a linear or branched $C_1$–$C_6$ alkoxy radical optionally comprising a silicon atom, a linear or branched $C_{1-5}$ alkoxycarbonyl group, or a linear or branched $C_1$–$C_6$ alkylsulfonamide group optionally comprising a silicon atom or an amino acid functional group, p' represents an integer between 0 and 4 inclusive, q' represents 0 or 1, $R_5$ represents hydrogen or an OH group, $R_6$ represents hydrogen, a linear or branched $C_1$–$C_6$ alkyl radical optionally comprising a silicon atom, a cyano group, a $C_1$–$C_6$ alkylsulfonyl radical or a phenylsulfonyl radical, $R_7$ represents a linear or branched $C_1$–$C_6$ alkyl radical optionally comprising a silicon atom or a phenyl group which can form a bicycle and which is optionally substituted by one or two $R_4$ radicals, or $R_6$ and $R_7$ together form a monocyclic, bicyclic or tricyclic $C_2$–$C_{10}$ hydrocarbonaceous residue, optionally interrupted by one or more nitrogen, sulfur and oxygen atoms and which can comprise another carbonyl, and optionally substituted by a linear or branched $C_1$–$C_8$ alkylsulfonamide group, and optionally comprising a silicon atom or an amino acid functional group; with the proviso that, when n'=1, $R_6$ and $R_7$ do not together form a camphor nucleus.

27. The cosmetic/dermatological UV-screening composition as defined by claim 26, said at least one aryl vinylene ketone UV-screening compound having the formula (10) in which n'=1.

28. The cosmetic/dermatological UV-screening composition as defined by claim 27, said at least one aryl vinylene ketone UV-screening compound comprising:
   a styryl ketone compound,
   a benzylidenecineole compound,
   a benzylidenechromanone compound,
   a benzylidenethiochromanone compound,
   a benzylidenequinuclidinone compound,
   a benzylidenecycloalkanone compound,
   a benzylidenehydantoin compound,
   a benzylideneindanone compound,
   a benzylidenetetralone compound,
   a benzylidenefuranone compound,
   a benzylidenebenzofuranone compound,
   a benzylideneindanedione compound,
   a benzylidenebenzothiofuranone compound,
   a benzylidenebarbituric compound,
   a benzylidenepyrazolone compound,
   a benzylideneimidazolone compound,
   a chalcone compound,
   a benzylidenone compound, and mixtures thereof.

29. The cosmetic/dermatological UV-screening composition as defined by claim 28, said at least one aryl vinylene ketone UV-screening compound comprising:
   1-(3,4-dimethoxyphenyl)-4,4-dimethylpent-1-en-3-one,
   1,3,3-trimethyl-5-(4-methoxybenzylidene)-2-oxa-bicyclo[2.2.2]octan-6-one,
   3-(4-methoxybenzylidene)-2,3,4a,8a-tetrahydrochromen-4-one;
   3-(4-methoxybenzylidene)-2,3,4a,8a-tetrahydrochromen-4-thione;
   4-methoxybenzylidene-1-azabicyclo[2.2.2]octan-3-one;
   2-(4-methoxybenzylidene)cyclopentanone and 2-(4-methoxybenzylidene)cyclohexanone;
   5-(3,4-dimethoxybenzylidene)imidazolidine-2,4-dione;
   2-(4-methoxybenzylidene)indan-1-one;
   2-(4-methoxybenzylidene)-3,4-dihydro-2H-naphthalen-1-one;
   4-(4-methoxybenzylidene)-2,2,5,5-tetramethyldihydrofuran-3-one;
   2-benzylidenebenzofuran-3-one;
   2-(3,5-di(tert-butyl)-4-hydroxybenzylidene)indane-1,3-dione;
   2-benzylidenebenzo[b]thiophen-3-one;
   5-(4-methoxybenzylidene)-1,3-dimethylpyrimidine-2,4,6-trione;
   4-(4-methoxybenzylidene)-5-methyl-2-phenyl-2,4-dihydropyrazol-3-one;
   5-(4-methoxybenzylidene)-2-phenyl-3,5-dihydro-imidazol-4-one;
   1-(2-hydroxy-4-methoxyphenyl)-3-phenylpropenone;
   3-hydroxy-1-(2-hydroxy-4-methoxyphenyl)-3-phenylpropenone, and mixtures thereof.

30. The cosmetic/dermatological UV-screening composition as defined by claim 26, said at least one aryl vinylene ketone UV-screening compound having the formula (10) in which n'=2.

31. The cosmetic/dermatological UV-screening composition as defined by claim 30, said at least one aryl vinylene ketone UV-screening compound comprising:
   a phenylenebis(methylidenenorcamphor) compound,
   a phenylenebis(methylidenecamphor) compound,
   a phenylenebis(methylidenecamphor-sulfonamide) compound,
   a phenylenebis(methylidenecineole) compound,
   a phenylenebis(methylideneketo-tricyclodecane) compound,
   a phenylenebis(alkylene ketone) compound,
   a phenylenebis(methylidenefuranone) compound,
   a phenylenebis(methylidene-quinuclidinone) compound, or mixture thereof.

32. The cosmetic/dermatological UV-screening composition as defined by claim 31, said at least one aryl vinylene ketone UV-screening compound comprising:
   1,4-phenylenebis{3-methylidenebicyclo[2.2.1]heptan-2-one},
   1,4-phenylenebis{3-methylidene-1,7,7-trimethyl-bicyclo[2.2.1]heptan-2-one} or
   1,3-phenylenebis-{3-methylidene-1,7,7-trimethylbicyclo[2.2.1]heptan-2-one},
   1,4-phenylenebis{3,3'-methylidenecamphor-10,10'-ethylsulfonamide or -(2-ethylhexyl)sulfonamide},
   1,4-phenylenebis{5-methylidene-3,3-dimethyl-2-oxa-bicyclo[2.2.2]octan-6-one},
   1,4-phenylenebis(octahydro-4,7-methano-6-inden-5-one),
   1,4-phenylenebis(4,4-dimethylpent-1-en-3-one),
   1,4-phenylenebis(4-methylidene-2,2,5,5-tetramethyl-dihydrofuran-3-one),
   1,4-phenylenebis{2-methylidene-1-azabicyclo[2.2.2]-octan-3-one}, or mixture thereof.

33. The cosmetic/dermatological UV-screening composition as defined by claim 26, said at least one aryl vinylene ketone UV-screening compound having the formula (11) and comprising a bis(benzylidene)cycloalkanone compound, a γ-pyrone compound, or mixture thereof.

34. The cosmetic/dermatological UV-screening composition as defined by claim 33, said at least one aryl vinylene ketone UV-screening compound having the formula (11) and comprising 2,5-di(benzylidene)cyclopentanone, 2,6-bis(3,4-dimethoxyphenyl)pyran-4-one, or mixture thereof.

35. The cosmetic/dermatological UV-screening composition as defined by claim 3, comprising at least one phenylenebis(benzoxazinone) UV-screening compound having the following formula (12):

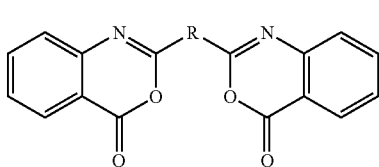

in which R is a divalent aromatic radical selected from among the following formulae (e″) to (h″):

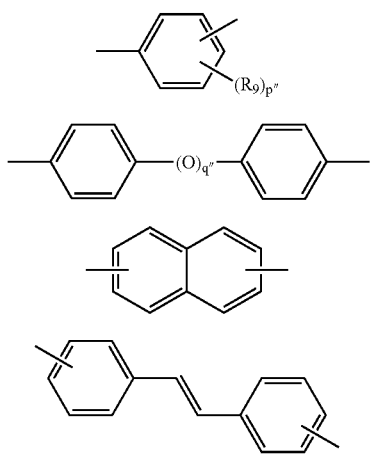

in which each of the $R_9$ symbols independently represents an OH group, a halogen atom, a linear or branched $C_1$–$C_6$ alkyl radical optionally comprising a silicon atom, a linear or branched $C_1$–$C_6$ alkoxy radical optionally comprising a silicon atom, a linear or branched $C_1$–$C_5$ alkoxycarbonyl radical, or a linear or branched $C_1$–$C_6$ alkylsulfonamide radical optionally comprising a silicon atom or an amino acid functional group, p″ represents an integer between 0 and 4 inclusive, and q″ represents 0 or 1.

36. The cosmetic/dermatological UV-screening composition as defined by claim 35, comprising at least one UV-screening compound of formula (12) selected from among:

2,2′-p-phenylenebis(3,1-benzoxazin-4-one), 2,2′-(4,4′-biphenylene)bis(3,1-benzoxazin-4-one), 2,2′-(2,6-naphthylene)bis(3,1-benzoxazin-4-one) and mixtures thereof.

37. The cosmetic/dermatological UV-screening composition as defined by claim 3, comprising at least one acrylonitrile amide, sulfonamide or carbamate UV-screening compound having the following formula (13):

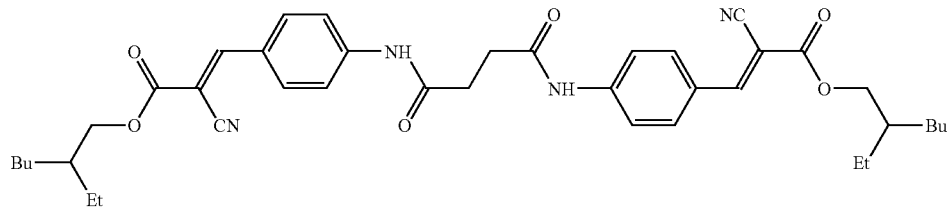

in which $R_{10}$ represents a linear or branched $C_1$–$C_8$ alkyl radical, n‴ has the value 0, 1 or 2, $X_2$ is a divalent radical of formula —(C=O)—$R_{11}$—(C=O)—, —$SO_2$—$R_{11}$—$SO_2$— or —(C=O)—O—$R_{11}$—O—(C=O)—, Y is a —(C=O)—$R_{12}$ or —$SO_2R_{13}$ radical, $R_{11}$ is a single bond or a linear or branched, divalent $C_1$–$C_{30}$ alkylene or $C_3$–$C_{30}$ alkenylene radical optionally substituted by one or more hydroxyl substituents and which can comprise, in the carbonaceous chain, one or more heteroatoms selected from among oxygen, nitrogen and silicon atoms, $R_{12}$ is an —$OR_{14}$ or —$NHR_{14}$ radical, $R_{13}$ is a linear or branched $C_1$–$C_{30}$ alkyl radical or a phenyl ring which is unsubstituted or substituted by $C_1$–$C_4$ alkyl or alkoxy radicals, $R_{14}$ is a linear or branched $C_1$–$C_{30}$ alkyl or $C_3$–$C_{30}$ alkenyl radical optionally substituted by one or more hydroxyl substituents and which can comprise, in the carbonaceous chain, one or more heteroatoms selected from among oxygen, nitrogen and silicon atoms; and isomers thereof.

38. The cosmetic/dermatological UV-screening composition as defined by claim 37, comprising at least one UV-screening dimer of 2-ethylhexyl 2-cyano-3-[4-(acetylamino)phenyl]acrylate having the formula:

39. The cosmetic/dermatological UV-screening composition as defined by claim 1, said at least one insoluble UV-screening agent comprising a polyvalent metal salt of sulfonic or carboxylic organic UV-screening agents.

40. The cosmetic/dermatological UV-screening composition as defined by claim 39, said insoluble UV-screening agents comprising polyvalent metal salts of sulfonated derivatives of benzylidenecamphor; polyvalent metal salts of sulfonated derivatives of benzimidazole; polyvalent metal salts of cinnamic acid derivatives, or mixtures thereof.

41. The cosmetic/dermatological UV-screening composition as defined by claim 1, said insoluble UV-screening agents comprising polyvalent metal or ammonium or substituted ammonium complexes of UV-A and/or UV-B organic screening agents.

42. The cosmetic/dermatological UV-screening composition as defined by claim 1, said at least one insoluble UV-screening agent comprising from 0.5% to 15% by weight thereof.

43. The cosmetic/dermatological UV-screening composition as defined by claim 42, said at least one insoluble UV-screening agent comprising from 1% to 10% by weight thereof.

44. The cosmetic/dermatological UV-screening composition as defined by claim 43, said at least one insoluble UV-screening agent comprising from 2% to 8% by weight thereof.

45. The cosmetic/dermatological UV-screening composition as defined by claim 1, said at least one 4,4-diarylbutadiene compound having the following formula (I):

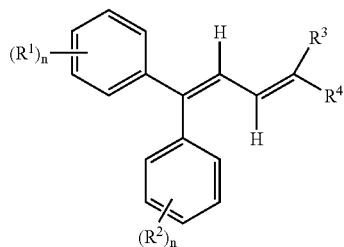

(I)

in which the diene system has the Z,Z; Z,E; E,Z or E,E configuration or is composed of mixtures of the said configurations, and wherein the radicals $R^1$ and $R^2$, which may be identical or different, are each hydrogen; a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical; a linear or branched $C_1$–$C_{20}$ alkoxycarbonyl radical; a linear or branched $C_1$–$C_{12}$ monoalkylamino radical; a linear or branched di($C_1$–$C_{12}$) alkylamino radical; an aryl radical; a heteroaryl radical or a water-solubilizing substituent which comprises a carboxylate group, a sulfonate group or an ammonium residue; $R^3$ is a $COOR^5$, $COR^5$, $CONR^5R^6$ or CN group; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; or a $C_3$–$C_7$ heteroaryl radical; $R^4$ is a $COOR^6$, $COR^6$, $CONR^5R^6$ or CN group; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; or a heteroaryl radical; the radicals $R^5$ and $R^6$, which may be identical or different, are each hydrogen; $[V]_o$—$R^7$, $C_1$–$C_6$-alkylene-$SO_3U$; $C_1$–$C_6$-alkylene-$PO_3U$; $C_1$–$C_6$-alkylene-$N(R^8)_3{}^+B'{}^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; or a heteroaryl radical; V is a —$CH_2$—$CH_2$—W—, —$CH_2CH_2CH_2W$—, —$CH(CH_3)$—$CH_2$—W—, —$CH_2$—$CH_2$—$CH_2$—$Ch_2$—W— or —$CH_2$—CH($CH_2CH_3$)—W— group; B' is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; W is O or NH; the radicals $R^7$ and $R^8$, which may be identical or different, are each hydrogen; a linear or branched $C_1$–$C_6$ alkyl radical; a linear or branched $C_2$–$C_6$ alkenyl radical; or a linear or branched $C_1$–$C_6$ acyl radical; $R^9$ is hydrogen; a linear or branched $C_1$–$C_6$ alkyl radical; or a $C_2$–$C_6$ alkenyl radical; n varies from 1 to 3; and o varies from 0 to 50.

46. The cosmetic/dermatological UV-screening composition as defined by claim 45, in which the compound of formula (I) has the following formula (Ia):

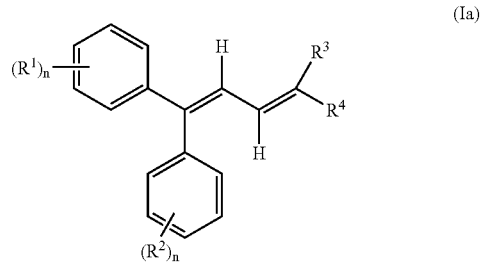

(Ia)

in which the diene system has the Z,Z; Z,E; E,Z or E,E configuration or is composed of mixtures of the said configurations, and wherein the radicals $R^1$ and $R^2$, which may be identical or different, are each hydrogen; a $C_1$–$C_8$ alkyl radical; a $C_1$–$C_8$ alkoxy radical; or a water-solubilizing substituent which comprises a carboxylate group, a sulfonate group or an ammonium residue; $R^3$ is a $COOR^5$, $CONR^5R^6$ or CN group; $R^4$ is a $COOR^6$ or $CONR^5R^6$ group; $R^5$ is hydrogen; $[V]_o$—$R^7$; $C_1$–$C_6$-alkylene-$SO_3U$; or $C_1$–$C_6$-alkylene-$N(R^8)_3{}^+B'{}^-$; $R^6$ is $[V]_o$—$R^7$; $C_1$–$C_6$-alkylene-$SO_3U$; or $C_1$–$C_6$-alkylene-$N(R^8)_3{}^+B'{}^-$; V is a —$CH_2$—$CH_2$—O—, —$CH_2CH_2CH_2O$— or —$CH(CH_3)$—$CH_2$—O— group; B' is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; the $R^9$, which may be identical or different, are each hydrogen or a linear or branched $C_1$–$C_3$ alkyl radical; o varies from 1 to 50; and n varies from 1 to 3.

47. The cosmetic/dermatological UV-screening composition as defined by claim 45, in which the compound of formula (I) has the following formula (Ib):

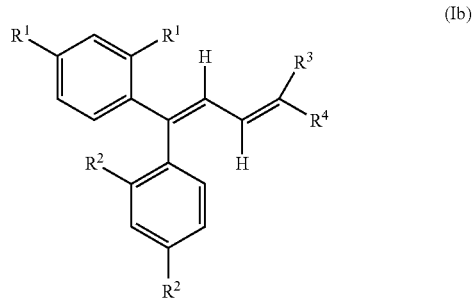

(Ib)

in which the diene system has the Z,Z; Z,E; E,Z or E,E configuration or is composed of mixtures of the said configurations, and wherein the radicals $R^1$ and $R^2$, which may be identical or different, are each hydrogen; a $C_1$–$C_8$ alkyl radical; or a $C_1$–$C_8$ alkoxy radical; $R^3$ is a $COOR^5$, $CONR^5R^6$ or CN group; $R^4$ is a $COOR^6$ or $CONR^5R^6$ group; $R^5$ is hydrogen; $[V]_o$—$R^7$; $C_1$–$C_6$-alkylene-$SO_3U$; or $C_1$–$C_6$-alkylene-$N(R^8)_3{}^+B'{}^-$; $R^6$ is $[V]_o$—$R^7$; $C_1$–$C_6$-alkylene-$SO_3U$; or $C_1$–$C_6$-alkylene-$N(R^8)_3{}^+B'{}^-$; V is a —$CH_2$—$CH_2$—O—, —$CH_2CH_2CH_2O$— group; B' is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which may be identical or different, are each hydrogen or a linear or branched $C_1$–$C_3$ alkyl radical; and o varies from 0 to 50.

48. The cosmetic/dermatological UV-screening composition as defined by claim 45, in which the compound of formula (I) has the following formula (Ic):

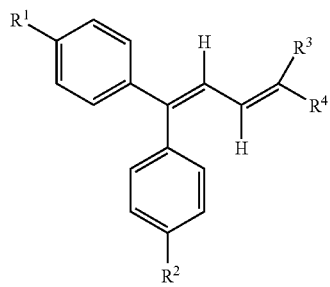

(Ic)

in which the diene system has the Z,Z; Z,E; E,Z or E,E configuration or is composed of mixtures of the said configurations, and wherein the radicals $R^1$ and $R^2$, which may be identical or different, are each hydrogen; a $C_1$–$C_8$ alkyl radical; or a $C_1$–$C_8$ alkoxy radical; $R^3$ is a $COOR^5$, $CONR^5R^6$ or CN group; $R^4$ is a $COOR^6$ or $CONR^5R^6$ group; $R^5$ is hydrogen; $[V]_o$–$R^7$; $C_1$–$C_6$-alkylene-$SO_3U$; or $C_1$–$C_6$-alkylene-$N(R^8)_3{}^+B'^-$; $R^6$ is $[V]_o$–$R^7$; $C_1$–$C_6$-alkylene-$SO_3U$; or $C_1$–$C_6$-alkylene-$N(R^8)_3{}^+B'^-$; V is a —$CH_2$—$CH_2$—O—, —$CH_2CH_2CH_2O$— or —$CH(CH_3)$—$CH_2$—O— group; B' is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which may be identical or different, are each hydrogen or a linear or branched $C_1$–$C_3$ alkyl radical; and o varies from 1 to 50.

49. The cosmetic/dermatological UV-screening composition as defined by claim 45, in which the compound of compound of formula (I) has the following formulae:

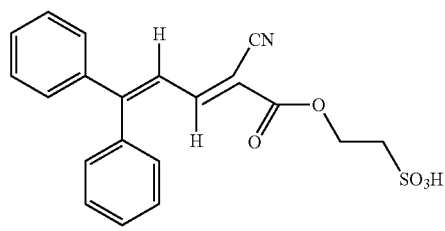

(10)

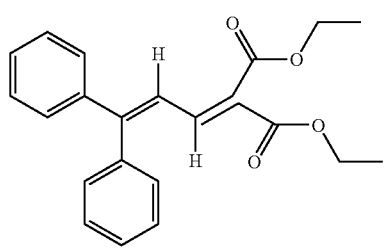

(11)

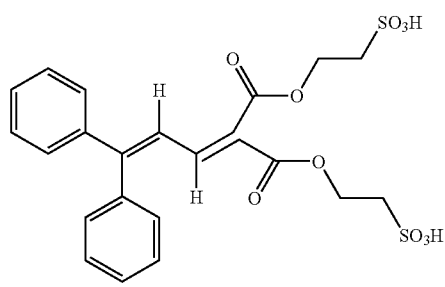

(12)

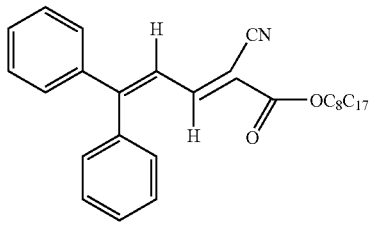

(13)

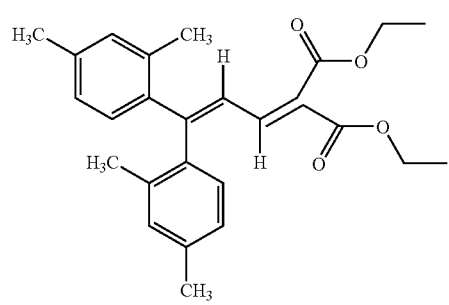

(14)

50. The cosmetic/dermatological UV-screening composition as defined by claim 1, said at least one 4,4-diarylbutadiene compound comprising an oligomer having the following formula (II):

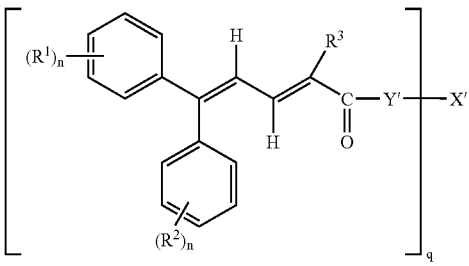

(II)

in which the diene system has the Z,Z; Z,E; E,Z or E,E configuration or is composed of mixtures of the said configurations, and wherein the radicals $R^1$, $R^2$, $R^3$ and n have the same meanings indicated in the formula (I); Y' is an —O— or —$NR^{10}$— group; $R^{10}$ is hydrogen; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cyclo-alkenyl radical; a $C_7$–$C_{10}$ bicycloalkenyl radical; an aryl radical; or a heteroaryl radical; X' is a linear or branched, aliphatic or cycloaliphatic, polyol residue comprising from 2 to 10 hydroxyl groups and with a valency of q; with the proviso that the carbonaceous chain of said residue may be interrupted by one or more sulfur or oxygen atoms; one or more imine groups; or one or more $C_1$–$C_4$ alkylimine groups; and q varies from 2 to 10.

51. The cosmetic/dermatological UV-screening composition as defined by claim 50, wherein formula (II) the radicals $R^1$ and $R^2$, which may be identical or different, are each hydrogen; a $C_1$–$C_{12}$ alkyl radical; a $C_1$–$C_8$ alkoxy radical; or a water-solubilizing substituent chosen from a carboxylate group, a sulfonate group or an ammonium residue; $R^3$ is a $COOR^5$, $CONR^5R^6$ or CN group; a $C_3$–$C_{10}$ cyclo-alkyl radical; or a $C_7$–$C_{10}$ bicycloalkyl radical; the radicals $R^5$ and $R^6$, which are identical or different, denote a linear or branched $C_1$–$C_{20}$ alkyl radical; a $C_3$–$C_{10}$ cyclo-alkyl radical;

a $C_7$–$C_{10}$ bicycloalkyl radical; or optionally substituted naphthyl or phenyl; and X' is a polyol residue comprising from 2 to 6 hydroxyl groups.

52. The cosmetic/dermatological UV-screening composition as defined by claim 51, wherein formula (II), X' is an ethanol or pentaerythritol residue.

53. The cosmetic/dermatological UV-screening composition as defined by claim 50, said compound of formula (II) being selected from among the following compounds:

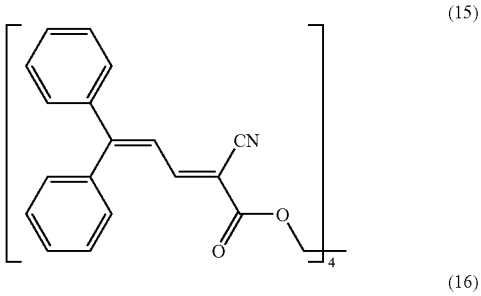

(15)

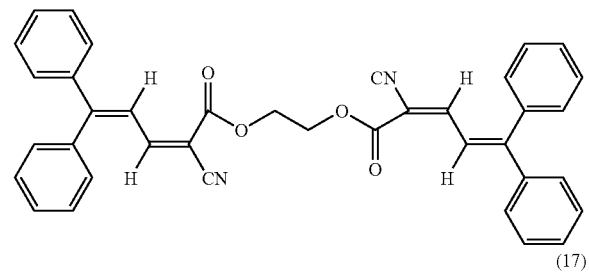

(16)

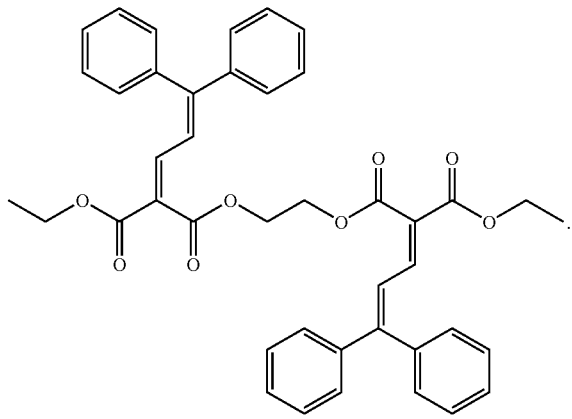

(17)

54. The cosmetic/dermatological UV-screening composition as defined by claim 1, said at least one 4,4-diarylbutadiene compound comprising from 0.5% to 15% by weight thereof.

55. The cosmetic/dermatological UV-screening composition as defined by claim 1, said at least one 4,4-diarylbutadiene compound comprising from 1% to 10% by weight thereof.

56. The cosmetic/dermatological UV-screening composition as defined by claim 1, said at least one 4,4-diarylbutadiene compound comprising from 0.5% to 15% by weight thereof.

57. The cosmetic/dermatological composition as defined by claim 1, further comprising at least one other UV-A-active and/or UV-B-active organic screening agent.

58. The cosmetic/dermatological composition as defined by claim 57, said at least one other organic UV-screening agent being selected from the group consisting of anthranilates; cinnamic derivative; salicylic derivatives; camphor derivatives; dibenzoylmethane derivatives; benzophenone derivatives; β,β'-diphenylacrylate derivatives; benzotriazole derivatives; benzalmalonate derivatives; triazine derivatives; benzimidazole derivatives; imidazolines; bis-benzazolyl derivatives; p-aminobenzoic acid (PABA) derivatives; methylenebis(hydroxyphenyl)benzotriazole derivatives; screening polymers and screening silicones; dimers derived from α-alkylstyrene and mixtures thereof.

59. The cosmetic/dermatological composition as defined by claim 58, said at least one other organic UV-screening agent being selected from the group consisting of:
Ethylhexyl salicylate,
Butyl Methoxydibenzoylmethane,
Ethylhexyl Methoxycinnamate,
Octocrylene,
Phenylbenzimidazole sulfonic acid,
Terephthalylidenedicamphorsulfonic acid,
Benzophenone-3,
Benzophenone-4,
Benzophenone-5,
4-Methylbenzylidenecamphor,
Disodium phenyl dibenzimidazole tetrasulfonate,
Benzimidazilate,
Anisotriazine,
Ethylhexyl triazone,
Diethylhexyl butamido triazone,
Drometrizole trisiloxane, and mixtures thereof.

60. The cosmetic/dermatological composition as defined by claim 1, further comprising at least one UV-screening coated or uncoated metal oxide pigment or nanopigment.

61. The cosmetic/dermatological composition as defined by claim 60, said at least one UV-screening pigment or nanopigment comprising titanium oxide, zinc oxide, iron oxide, zirconium oxide, cerium oxide, and mixtures thereof.

62. The cosmetic/dermatological composition as defined by claim 1, further comprising at least one agent for artificially tanning and/or browning the skin.

63. The cosmetic/dermatological composition as defined by claim 1, further comprising at least one adjuvant or additive selected from the group consisting of fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preservatives, surfactants, anti-inflammatories, substance P antagonists, fillers, polymers, propellants, acidifying or basifying agents, colorants, and mixtures thereof.

64. The cosmetic/dermatological composition as defined by claim 1, formulated for photoprotecting the human epidermis and comprising a nonionic vesicular dispersion, an emulsion, a cream, a milk, a gel, a cream-gel, a suspension, a dispersion, a powder, a solid, a mousse or a spray.

65. The cosmetic/dermatological composition as defined by claim 1, formulated as a makeup for the eyelashes, the eyebrows or the skin and comprising a solid or pasty, anhydrous or aqueous formulation, or an emulsion, a suspension or a dispersion.

66. The cosmetic/dermatological composition as defined by claim 1, formulated for photoprotecting the hair against ultraviolet rays and comprising a shampoo, a lotion, a gel, an emulsion or a nonionic vesicular dispersion.

67. A regime or regimen for photoprotecting the skin and/or hair against the damaging effects of UV radiation, comprising topically applying thereon an effective amount of the cosmetic/dermatological UV-screening composition as defined by claim 1.

68. A method for synergistically enhancing the SPF of particulates of at least one insoluble organic UV-screening agent having a particle size ranging from 10 nm to 5 µm, comprising formulating therewith an effective amount of at least one 4,4-diarylbutadiene compound.

* * * * *